(12) United States Patent
Johnston et al.

(10) Patent No.: US 8,969,255 B2
(45) Date of Patent: Mar. 3, 2015

(54) COMPOUND ARRAYS FOR SAMPLE PROFILING

(71) Applicant: The Arizona Board of Regents, a body corporate of the State of Arizona acting for and on behalf of Arizona State University, Scottsdale, AZ (US)

(72) Inventors: Stephen Albert Johnston, Tempe, AZ (US); Phillip Stafford, Phoenix, AZ (US)

(73) Assignee: The Arizona Board of Regents, Scottsdale, AZ (US), A Body Corporate of the State of Arizona, Acting for and on the Behalf of Arizona State University ( * ) Notice: Subject to any disclaimer, the term of this patent is extended or adjusted under 35 U.S.C. 154(b) by 0 days.

(21) Appl. No.: 13/683,778

(22) Filed: Nov. 21, 2012

(65) Prior Publication Data
US 2013/0143756 A1 Jun. 6, 2013

Related U.S. Application Data

(62) Division of application No. 13/379,080, filed as application No. PCT/US2010/039269 on Jun. 18, 2010.

(60) Provisional application No. 61/249,147, filed on Oct. 6, 2009, provisional application No. 61/218,890, filed on Jun. 19, 2009.

(51) Int. Cl.
| | |
|---|---|
| C40B 30/04 | (2006.01) |
| G01N 33/53 | (2006.01) |
| G01N 33/543 | (2006.01) |
| G01N 33/558 | (2006.01) |
| G01N 33/68 | (2006.01) |
| C40B 40/10 | (2006.01) |

(52) U.S. Cl.
CPC ........ *G01N 33/543* (2013.01); *G01N 33/54306* (2013.01); *G01N 33/6845* (2013.01); *G01N 33/6854* (2013.01); *G01N 33/53* (2013.01); *C40B 40/10* (2013.01)
USPC ................ 506/9; 435/7.1; 436/514; 436/518

(58) Field of Classification Search
CPC .... A61B 5/14546; C07K 17/02; C07K 17/14; C40B 40/10; C40B 30/04; G01N 33/49; G01N 33/50; G01N 33/5005; G01N 33/53; G01N 33/5308; G01N 33/543; G01N 33/6854; G01N 2033/53
See application file for complete search history.

(56) References Cited

U.S. PATENT DOCUMENTS

| | | | |
|---|---|---|---|
| 5,143,854 A | 9/1992 | Pirrung | |
| 5,571,639 A | 11/1996 | Hubbell | |
| 5,593,839 A | 1/1997 | Hubbell | |
| 5,595,915 A | 1/1997 | Geysen | |
| 5,677,195 A | 10/1997 | Winkler et al. | |
| 5,919,523 A | 7/1999 | Sundberg et al. | |
| 6,083,763 A | 7/2000 | Balch | |
| 6,309,831 B1 | 10/2001 | Goldberg et al. | |
| 6,329,209 B1 | 12/2001 | Wagner et al. | |
| 6,346,413 B1 | 2/2002 | Fodor et al. | |
| 6,359,125 B1 | 3/2002 | Kim et al. | |
| 6,365,418 B1 | 4/2002 | Wagner et al. | |
| 6,387,631 B1 | 5/2002 | Arnold et al. | |
| 6,399,365 B2 | 6/2002 | Besemer et al. | |
| 6,465,183 B2 | 10/2002 | Wolber | |
| 6,475,808 B1 | 11/2002 | Wagner et al. | |
| 6,475,809 B1 | 11/2002 | Wagner et al. | |
| 6,489,159 B1 | 12/2002 | Chenchik et al. | |
| 6,496,309 B1 | 12/2002 | Bliton et al. | |
| 6,511,277 B1 | 1/2003 | Norris et al. | |
| 6,545,748 B1 | 4/2003 | Trozera | |
| 6,567,163 B1 | 5/2003 | Sandstrom | |
| 6,569,671 B1 | 5/2003 | Okamoto et al. | |
| 6,573,369 B2 | 6/2003 | Henderson et al. | |
| 6,604,902 B2 | 8/2003 | Norris et al. | |
| 6,620,584 B1 | 9/2003 | Chee | |
| 6,630,358 B1 | 10/2003 | Wagner et al. | |
| 6,660,479 B2 | 12/2003 | Kim et al. | |
| 6,706,875 B1 | 3/2004 | Goldberg et al. | |

(Continued)

FOREIGN PATENT DOCUMENTS

| | | |
|---|---|---|
| EP | 624059 | 5/1993 |
| EP | 476014 | 8/1994 |

(Continued)

OTHER PUBLICATIONS

Miseta, Attila et al. 2000 Mol Biol Evol 17: 1232-1239.*
Geysen, Mario H. et al 1984 PNAS 81: 3998-4002.*
Merbl et al Jun. 2009 PLoS ONE 4: e6053.*
Quintana et al 2006 Lupus 15: 428-430.*
U.S. Appl. No. 13/425,181, filed Mar. 20, 2012 ( Reissue application of US Patent 7,682,797).
U.S. Appl. No. 13/624,332 Office action mailed Jan. 22, 2013.
U.S. Appl. No. 13/624,386 Office action mailed Jan. 23, 2013.
U.S. Appl. No. 13/379,080 Office action mailed Oct. 11, 2012.
U.S. Appl. No. 13/379,080 Final Office action mailed Apr. 8, 2013.

(Continued)

*Primary Examiner* — Christopher M Gross
*Assistant Examiner* — Christopher Reyes
(74) *Attorney, Agent, or Firm* — Wilson Sonsini Goodrich & Rosati

(57) ABSTRACT

The invention provides arrays of compound for use in profiling samples. The arrays include compounds bind to components of the samples at relatively low affinities. The avidity of compounds binding to components of the samples can be increased by forming arrays such that multivalent components of the samples (e.g., antibodies or cells) can bind to more than one molecule of a compound at the same time. When a sample is applied to an array under such conditions, the compounds of the array bind to component(s) of the sample with significantly different avidities generating a profile characteristic of the sample.

33 Claims, 13 Drawing Sheets

(56) References Cited

U.S. PATENT DOCUMENTS

| | | |
|---|---|---|
| 6,723,517 B1 | 4/2004 | Bamdad |
| 6,733,977 B2 | 5/2004 | Besemer et al. |
| 6,780,582 B1 | 8/2004 | Wagner et al. |
| 6,806,954 B2 | 10/2004 | Sandstrom |
| 6,824,669 B1 | 11/2004 | Li et al. |
| 6,877,665 B2 | 4/2005 | Challa et al. |
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |
| 7,081,954 B2 | 7/2006 | Sandstrom |
| 7,108,472 B2 | 9/2006 | Norris et al. |
| 7,130,458 B2 | 10/2006 | Bartell |
| 7,148,058 B2 | 12/2006 | Charych et al. |
| 7,247,469 B2 | 7/2007 | Wagner et al. |
| 7,354,721 B2 | 4/2008 | Tchaga |
| 7,466,851 B2 | 12/2008 | Gulati |
| 7,522,271 B2 | 4/2009 | Sandstrom |
| 7,534,563 B2 | 5/2009 | Hargreaves |
| 7,569,343 B2 | 8/2009 | Marton et al. |
| 7,588,906 B2 | 9/2009 | Bruegemeier et al. |
| 7,622,295 B2 | 11/2009 | Cabezas |
| 7,682,797 B2 | 3/2010 | Thompson et al. |
| 7,682,798 B2 | 3/2010 | Thompson et al. |
| 7,695,919 B2 | 4/2010 | Apel et al. |
| 7,723,125 B2 | 5/2010 | Tchaga |
| 7,993,583 B2 | 8/2011 | Dugan et al. |
| 8,073,626 B2 | 12/2011 | Troup et al. |
| 8,148,141 B2 | 4/2012 | Nokihara et al. |
| 8,242,058 B2 | 8/2012 | Raines et al. |
| RE44,031 E | 2/2013 | Apel et al. |
| 2003/0082579 A1 | 5/2003 | Feigner et al. |
| 2003/0207467 A1 | 11/2003 | Synder et al. |
| 2004/0038307 A1 | 2/2004 | Lee et al. |
| 2004/0048311 A1 | 3/2004 | Ault-Riche |
| 2004/0071705 A1 | 4/2004 | Sato et al. |
| 2005/0009204 A1 | 1/2005 | Fang |
| 2005/0048566 A1 | 3/2005 | Delisi et al. |
| 2005/0064395 A1 | 3/2005 | Israel |
| 2005/0255491 A1 | 11/2005 | Lee et al. |
| 2007/0003954 A1 | 1/2007 | Kodadek |
| 2007/0015172 A1 | 1/2007 | Zhang et al. |
| 2007/0099256 A1 | 5/2007 | Sundararajan et al. |
| 2008/0193965 A1 | 8/2008 | Zeng et al. |
| 2009/0131278 A1 | 5/2009 | Wagner et al. |
| 2010/0035765 A1 | 2/2010 | Kodadek |
| 2011/0046015 A1 | 2/2011 | Honda et al. |
| 2011/0065594 A1 | 3/2011 | Thompson et al. |
| 2011/0190149 A1 | 8/2011 | Tainsky et al. |
| 2011/0275537 A1 | 11/2011 | Rychlewski et al. |
| 2011/0301057 A1 | 12/2011 | Propheter |
| 2011/0301058 A1 | 12/2011 | Cheng et al. |
| 2012/0189702 A1 | 7/2012 | Gupta |
| 2012/0190574 A1 | 7/2012 | Johnston et al. |
| 2012/0238477 A1 | 9/2012 | Albert et al. |
| 2013/0079242 A1 | 3/2013 | Johnston et al. |
| 2013/0079250 A1 | 3/2013 | Johnston et al. |

FOREIGN PATENT DOCUMENTS

| | | |
|---|---|---|
| EP | 728520 | 8/1996 |
| EP | 1785726 | 5/2007 |
| WO | WO91/18980 | 12/1991 |
| WO | WO93/06121 | 4/1993 |
| WO | WO94/08051 | 4/1994 |
| WO | WO95/12608 | 5/1995 |
| WO | WO95/30642 | 11/1995 |
| WO | WO95/35503 | 12/1995 |
| WO | WO2007/147141 | 12/2007 |
| WO | WO2008/048970 | 4/2008 |
| WO | WO 2008-048970 | 4/2008 |
| WO | WO 2008/085185 A2 | 7/2008 |
| WO | WO2008/151146 | 12/2008 |
| WO | WO2009/140039 | 11/2009 |

OTHER PUBLICATIONS

Berglund, Lisa, et al. "A Genecentric Human Protein Atlas for Express Profiles Based on antibodies." Oct. 1, 2008, Molecular and Cellular Proteomics, 7, pp. 2019-2027.

Bailey. Meme: discovering and analyzing DNA and protein sequence motifs. (2006) Nucleic Acids Res. 34(suppl 2): W369-W373.

Breitling. High-density peptide arrays. (2009) Mol. BioSyst., 5: 224-234.

Cretich. Protein and peptide arrays: Recent trends and new directions, (2006) Biomol. Eng. 23: 77-88 (2006).

EP 10790305.6 Extended European Search Report dated Aug. 20, 2013.

Fodor. Multiplexed biochemical assays with biological chips. (1993) Nature 364: 555-556.

Frith. Discovering Sequence Motifs with Arbitrary Insertions and Deletions. (2008) PLOS Comput. Blol. 4: e1000071.

Jonassen. Efficient discovery of conserved patterns using a pattern graph. (1997) Comput. Appl. Biosci. 13: 509-22.

Legutki. A general method for characterization of humoral immunity induced by a vaccine or infection. (2010) Vaccine 28(28): 4529-37.

Min. Peptide arrays: towards routine implementation. (2004) Current Opinion in Chemical Biology 8: 554-558.

Reddy et al., Protein fingerprinting in complex mixtures with peptoid microarrays, Proc. of the Nat'l Academy of Sciences, Nat'l Academy of Sciences, US, 102(36):12672-12677 Sep. 2005.

Rigoutsos. In Silico Pattern-Based Analysis of the Human Cytomegalovirus Genome. (1998) Bioinformatics 14: 55-67.

U.S. Appl. No. 13/624,332 Final action mailed Sep. 20, 2013.

U.S. Appl. No. 13/624,386 Final action mailed Sep. 20, 2013.

U.S. Appl. No. 13/379,080 Final Office action mailed Oct. 3, 2013.

Neuman de Vegvar, et al. "Microarray profiling of antiviral antibodies for the development of diagnostics, vaccines, and therapeutics" Clinical Immunology vol. 111 (2004) pp. 196-201.

Quintana, et al. "The Natural autoantibody repertoire and autoimmune disease" Biomedicine & Pharmacotheraphy vol. 58 (2004) pp. 276-281.

Reineke, et al. "Identification of Distinct Antibody Epitopes and mimotopes from a peptide array of 5520 randomly generated sequences" Journal of Immunological Methods vol. 267 (2002) pp. 37-51.

U.S. Appl. No. 13/624,332 Advisory Action mailed Mar. 4, 2014.

U.S. Appl. No. 13/624,386 Advisory Action mailed Mar. 4, 2014.

U.S. Appl. No. 13/379,080 Advisory Action mailed Mar. 4, 2014.

U.S. Appl. No. 13/379,080 Non-Final Office action mailed Sep. 12, 2014.

* cited by examiner

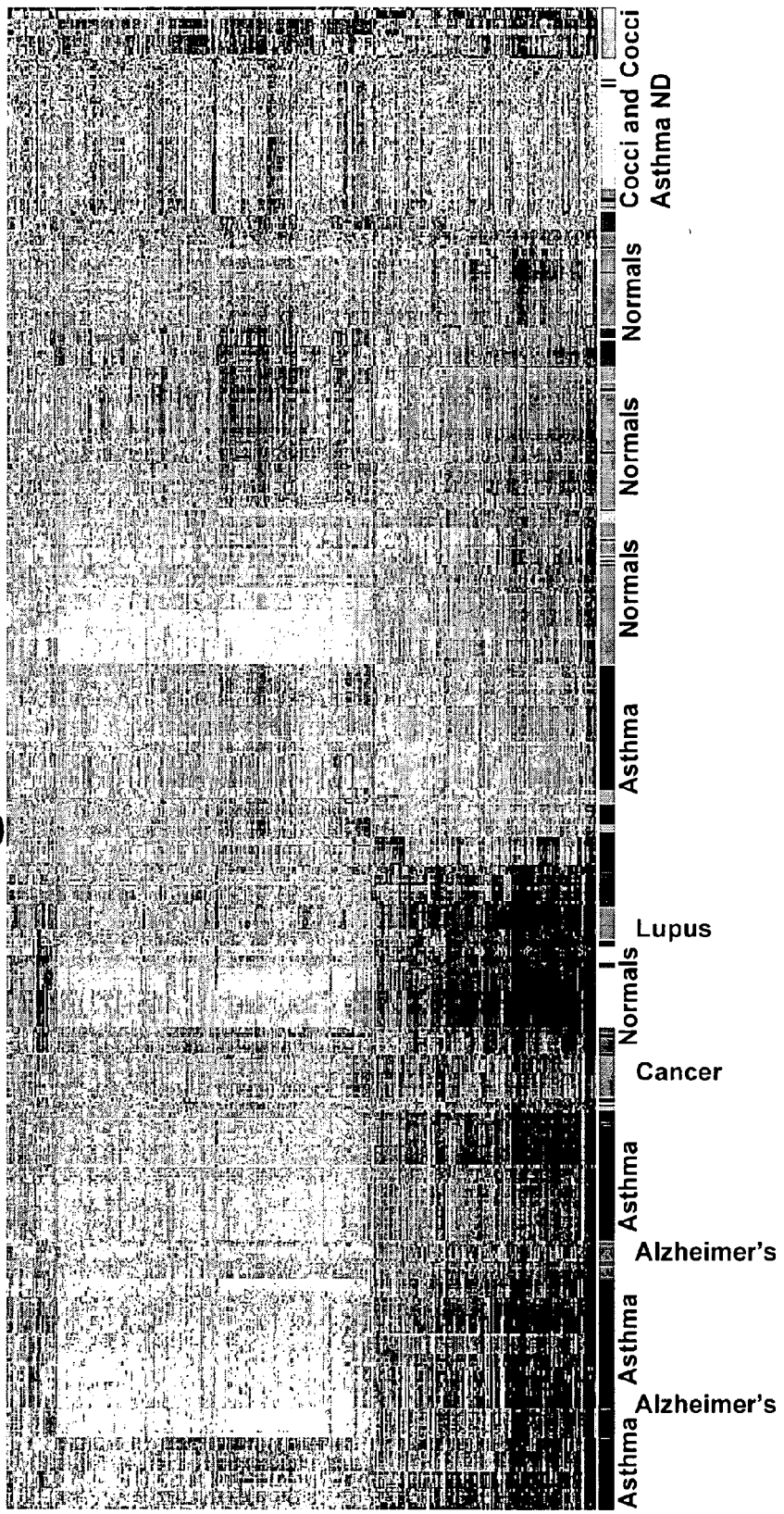

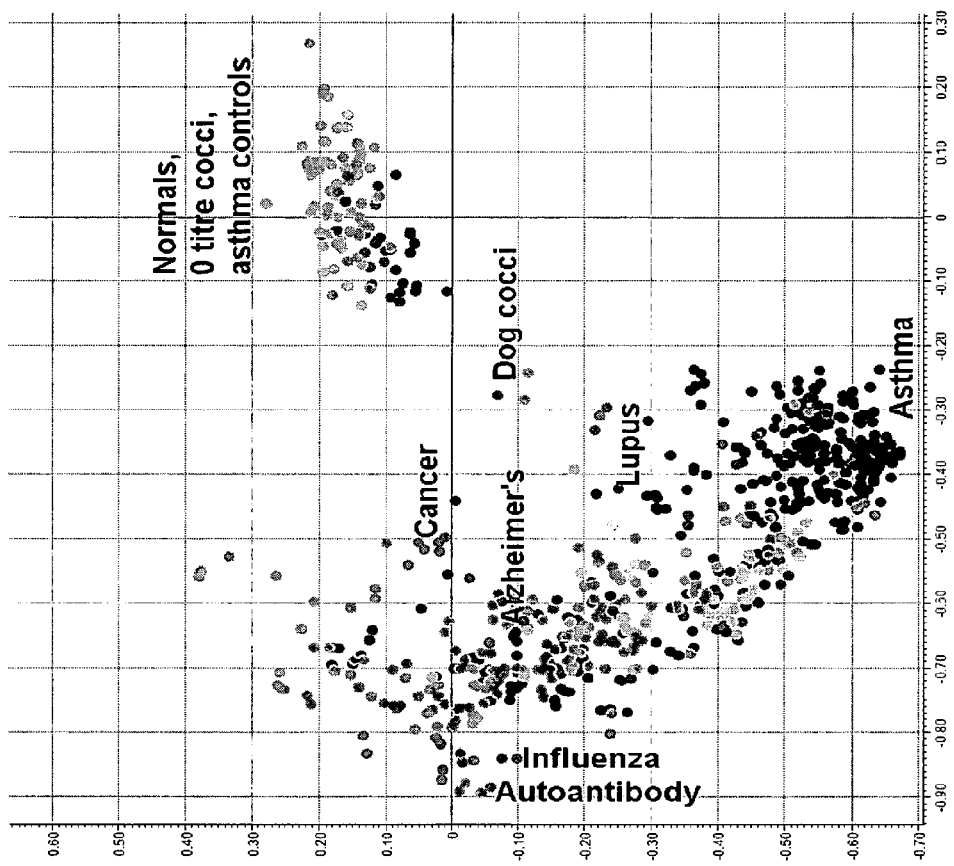

COMPOUND ARRAYS FOR SAMPLE PROFILING

CROSS-REFERENCE TO RELATED APPLICATIONS

The present application is a divisional of U.S. Ser. No. 13/379,080, filed Jan. 18, 2012; which is a 371 U.S. National Phase Application of PCT/US2010/039269, filed Jun. 18, 2010; which claims the benefit of U.S. Ser. No. 61/218,890, filed Jun. 19, 2009; and U.S. Ser. No. 61/249,147 filed Oct. 6, 2009; all of which are incorporated by reference in their entirety for all purposes.

BACKGROUND OF THE INVENTION

ELISA reactions and other simple immunoassays are commonly used for diagnosing disease. Many assays are configured to detect a single analyte. Therefore, when several differential diagnoses are possible, several different such assays are often conducted in parallel.

Existing approaches for broadly characterizing an immune response involve multiple standard ELISAs, use of library panning involving multiple rounds of selection, or printing of known proteins from pathogens or host proteins in an array format to detect antibodies to pathogens or autoantibodies. T-cells and B-cells have also been characterized by isolating and cloning specific regions of the T- and B-cell genome to sequence the recombination event. All of these processes are labor intensive and take time. They are not conducive to a standard clinical diagnostic protocol or early detection before specific analytes for which specific binding reagents are provided.

SUMMARY OF THE INVENTION

The invention provides methods of analyzing a sample, comprising: (a) contacting the sample with an array of immobilized different compounds occupying different areas of the array, wherein different molecules of the same compound within an area are spaced sufficiently proximate to one another for multivalent binding between at least two of the different molecules in the same area and a multivalent binding partner; and (b) detecting binding of the different compounds in the array to component(s) of the sample, such as antibodies. The sample can thus be characterized from the relative binding of compounds whose binding to the sample would be difficult to distinguish from each other and nonspecific binding under conditions of monovalent binding but which show significantly different binding from each other and nonspecific binding due to multivalent binding of the sample to the compounds thereby generating a binding profile characteristic of the sample.

In some methods, the sample is characterized from the relative binding a plurality of the sample that binds to the different compounds binding to the sample with association constants of 1 mm to 1 µM. In some methods, the sample is characterized from the relative binding of at least 10 or 100 compounds binding to the sample with association constants of 1 mm to 1 µM. In some methods, the sample is characterized by comparing a binding profile of the sample that includes the relative binding of the plurality of compounds with a reference binding profile. In some methods, the average spacing between molecules of a compound in an area of the array is less than 6 nm.

Optionally, the method further comprises identifying a component of the sample that binds to the different compounds. Optionally, the method further comprises detecting the identified component with a binding partner known to bind the component. Optionally, the identified component is detected with a plurality of different binding partners known to bind the component. Optionally, the binding partner is an antibody to the identified component. Optionally, the binding partner is a peptide known to bind the identified component. Optionally, the binding partner is one of the different compounds detected in step (b). Optionally, the binding partner is a synbody. Optionally, the binding partner is immobilized to a support. Optionally, the binding partner is immobilized to a support in an array. Optionally, the method further comprises forming a second array, the second array containing one or more of the different compounds in the array binding to identified component not all of the different compounds in the array. Optionally, the second array contains less than 5% of the different compounds in the array. Optionally, the method further comprises forming an array or other device comprising compounds determined to bind to the sample but not all of the different compounds in the array.

In some methods, the detecting step detects binding of the different compounds to an antibody or antibodies in the sample. In some methods, the detecting step detects binding of the different compounds to a biological entity displaying multiple copies of a protein from its outer surface. In some methods, the biological entity is cell displaying multiple copies of receptor from its outersurface. In some methods, the compound having strongest binding to the sample binds to the component of the sample to which it has strongest binding affinity with an avidity of 0.1 µM to 1 mM. In some methods, the compounds are peptides or small molecules. In some methods, the array has 500-50,000 peptides. In some methods, the peptides are 10-30 amino acid long. In some methods, the sequences of the peptides are randomly selected. In some methods, the different immobilized compounds are selected without regard to the sample and the array further comprises a plurality of compounds known to bind different proteins also occupying different areas of the array. In some methods, the plurality of compounds known to bind different proteins includes compounds known to bind at least 25%, 50 or 75% of different human proteins. In some methods, the different immobilized compounds including a plurality of compounds known to bind at least 25%, 50% or 75% of different human proteins and 500-50,000 random peptides. In some methods, the sequences of the peptides have less than 90% sequence identity to a known binding partner of the target. In some methods, the sequences of the peptides have less than 90% sequence identity to known proteins. In some methods, the average spacing between compounds in an area of the array is 2-4 nm. In some methods, the average spacing between compounds in an area of the array is 3 nm. In some methods, the contacting of the sample to the array is performed in the presence of a potential competitor of binding of the sample to the array. In some methods, the competitor is a known binding partner of a suspected component of the sample.

In some methods, the sample is a patient sample, and the competitor is a protein known to be associated with a disease affecting the patient. In some methods, the sample is a patient sample. In some methods, the sample contains a plurality of antibodies. In some methods, the patient is known or suspected to be suffering from a disease. In some methods, the patient is known to be at risk of a disease but is not showing symptoms of the disease. In some the disease is an autoimmune disease, an infectious disease, or a disease of the CNS. In some methods, the sample is a blood, urine, or CNS sample. In some methods, component(s) of the sample are labeled. In some methods, binding of the peptides to component(s) of the sample is detected using a secondary antibody. In some methods, the secondary antibody is an isotype-specific antibody. In some methods, binding of the peptides to component(s) of the sample is detected by spr or mass spectrometry.

Some methods further comprise affinity purifying a component of the sample using a peptide determined to bind to the sample. Some methods further comprise washing unbound component(s) of the sample from the array, and dissociating bound component(s) from the array. Some methods further comprise preparing an antibody library from the patient and using a peptide to which an antibody in the sample binds as an affinity reagent to screen the library. Some methods further comprise identifying a natural binding partner of the affinity purified antibody. Some methods further comprise comparing the sequence(s) of peptide(s) binding to the component(s) of the sample to a database of natural sequences to identify natural binding partner(s) of components of the sample. Some methods further comprise comparing a profile of different compounds binding to the sample with profiles of the different compounds associated with different diseases or different stages of a disease to diagnose a patient as having one of the diseases or stages of disease. Some methods further comprise comparing a profile of different compounds binding to the sample with a profile of the different compounds associated with lack of a disease to determine whether a disease is present. Some methods further comprise repeating the method for different samples from a plurality of patients with the same disease to develop a binding profile characteristic of the disease. Some methods further comprise repeating the method for different samples from a plurality of patients with different disease to develop a plurality of binding profiles characteristic of different diseases.

The invention further provides an array of immobilized different compounds occupying different areas of the array, wherein different molecules of the same compound within an area are spaced sufficiently proximate to one another for multivalent binding between at least two of the different molecules in the same area and a multivalent binding partner.

The invention further provides methods of analyzing a sample, comprising: contacting the sample with an array of immobilized different peptides occupying different areas of the array; detecting binding of the different peptides in the array to component(s) of the sample; and characterizing the sample from the relative binding of a plurality of peptides with apparent dissociation constants between 1 mM and 1 µM for the sample. Optionally, the sample is characterized from the relative binding of at least ten peptides with apparent dissociation constants between 1 mM and 1 µM.

The invention further provides a method of characterizing a plurality of different samples, comprising contacting the different samples with the same array or copies of the same array of immobilized different peptides occupying different areas of the array; and detecting different binding profiles of the different peptides to the different samples; wherein the samples are characterized from their respective binding patterns. Optionally, the plurality of different samples includes samples from patients with different disease symptoms. Optionally, the plurality of different samples includes samples of patients presenting with disease and lack of disease.

The invention further provides a method of analyzing a sample, comprising: contacting the sample with an array of immobilized different compounds occupying different areas of the array, wherein different molecules of the same compound within an area are spaced at an average distance of less than 4 nm apart in the same area; and detecting binding of the different compounds in the array to component(s) of the sample.

The invention further provides a method of analyzing a sample, comprising (i) contacting a sample with a known binding partner of a component of the sample; and (ii) determining whether the binding partner binds to the sample compared with a control lacking the component; wherein the known binding partner is identified by a process comprising (a) contacting an initial sample with an array of immobilized different compounds occupying different areas of the array, wherein different molecules of the same compound within an area are spaced sufficiently proximate to one another for multivalent binding between at least two of the different molecules in the same area and a multivalent binding partner; and (b) detecting binding of the different compounds in the array to component(s) of the sample; (c) identifying a component of the sample that binds to the different compounds; and (d) identifying a known binding partner of the component for use in step (i).

Optionally, the component in step (i) is detected with a plurality of different binding partners known to bind the component. Optionally, the binding partner is an antibody to the component. Optionally, the binding partner is a peptide known to bind the component. Optionally, the binding partner is one of the different compounds detected in step (b). Optionally, the binding partner is the binding partner is immobilized to a support in an array in step (i).

The invention further provides a method of manufacturing a device for use in detecting a component of a sample comprising: (a) contacting the sample with an array of immobilized different compounds occupying different areas of the array, wherein different molecules of the same compound within an area are spaced sufficiently proximate to one another for multivalent binding between at least two of the different molecules in the same area and a multivalent binding partner; and (b) detecting binding of the different compounds in the array to component(s) of the sample; and (c) forming a device including a known binding partner of a component to which binding of the different compounds is detected in step (b).

Some methods further comprise identifying the component of the sample that binds to the different compounds. Some methods further comprise forming the device including a plurality of different binding partners known to bind the component. Optionally, the binding partner is an antibody to the component. Optionally, the binding partner is a peptide known to bind the component. Optionally, the binding partner is one of the different compounds detected in step (b). Optionally, the binding partner is a synbody. Optionally, the binding partner is immobilized to a support. Optionally, the binding partner is immobilized to a support in an array. Optionally, step (c) comprises forming a second array, the second array containing one or more of the different compounds in the array binding to the second array contains less than 5% of the different compounds in the array.

The invention further provides a method of testing a vaccine, comprising contacting a blood sample of a subject immunized with a vaccine against a pathogenic microorganism with an array of immobilized different compounds occupying different areas of the array; detecting a pattern of binding of the sample to the different compounds in the array; and comparing the pattern of binding to the pattern of binding of one or more reference samples, wherein the reference samples are from subjects who have survived an infection with the virus, similarity of binding profile between the subject and reference samples providing an indication the vaccine is effective against the pathogenic microorganism. Optionally, the subjects have been immunized with a vaccine before exposure to the virus.

The invention further provides an array of immobilized different compounds occupying different areas of the array, wherein the different compounds include a plurality of compounds known to bind at least 25, 50 or 75% of the known human proteins and 500-1,000,000 or more random peptides, wherein different molecules of the same peptide within an area are spaced sufficiently proximate to one another for multivalent binding between at least two of the different molecules in the same area and a multivalent binding partner.

The invention further provides a method of analyzing a sample, comprising contacting the sample with an array of immobilized different compounds occupying different areas of the arrays; detecting binding of the different compounds in the array to component(s) of the sample; and characterizing the sample from the relative binding of a plurality of compounds having binding strengths to the sample greater than but within three orders of magnitude of the mean plus three standard deviations of the binding strength of empty areas in the array. Optionally, the characterizing comprising comparing a binding profile of the sample including the plurality of compounds with a reference binding profile including the plurality of compounds. Optionally, the sample is characterized from the relative binding of at least 10 or 100 compounds having binding strengths to the sample greater than but within three orders of magnitude of the mean plus three standard deviations of the binding strength of empty areas in the array.

BRIEF DESCRIPTION OF THE DRAWINGS

FIG. 9A is that antibody detecting PR8 particles.

FIG. 10A shows a hierarchical clustering of 875 different individual samples and 2000 different peptides indicating that patients with different diseases show a common pattern of binding per disease. FIG. 10B shows principal component maps for the same peptides and provides a view of the degree of separation between samples.

DEFINITIONS

Figure 1:
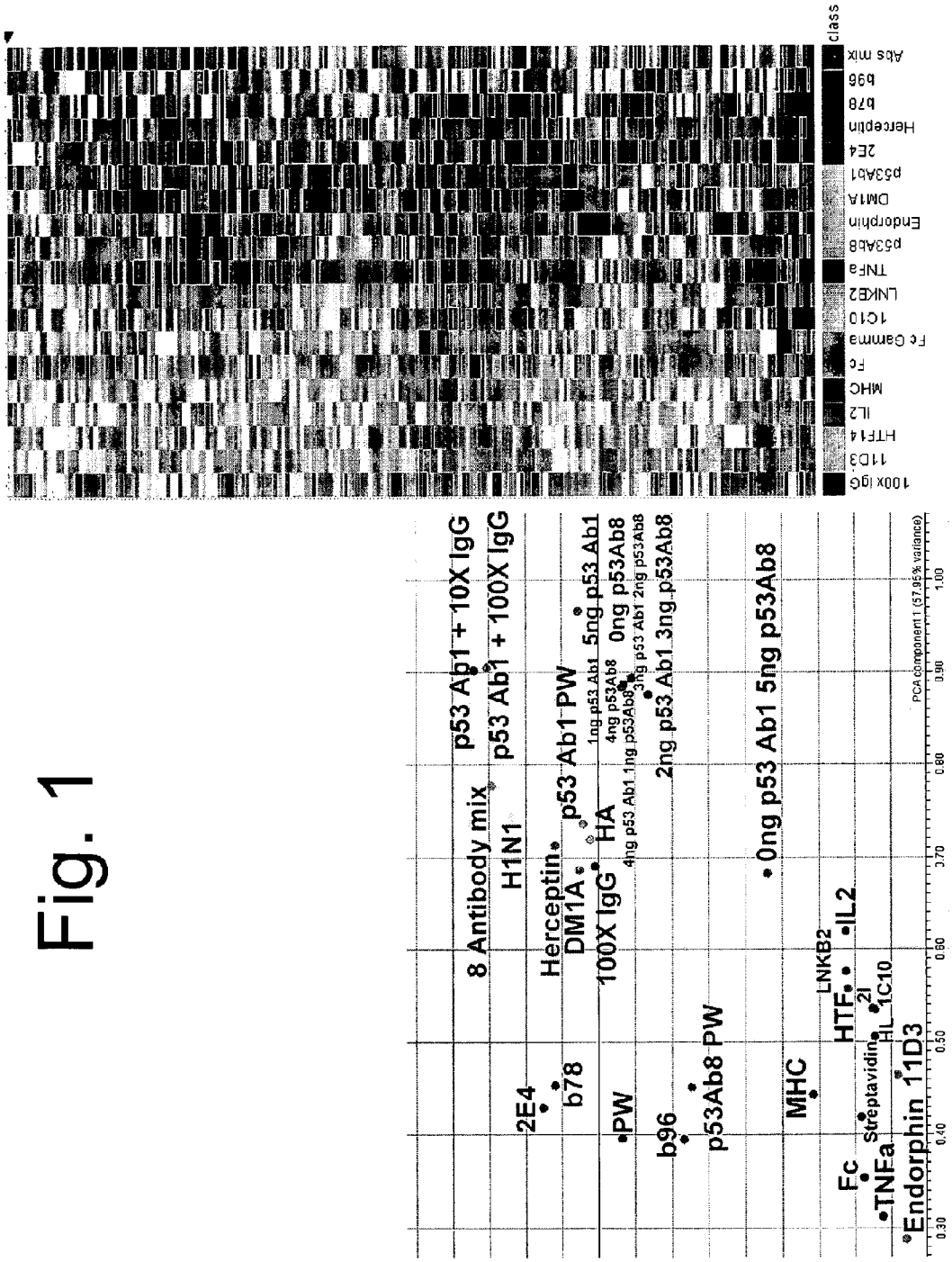
FIG. 1 shows binding of 800 peptides to various antibodies and the degree of separation of these antibodies.

Specific binding refers to the binding of a compound to a target (e.g., a component of a sample) that is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however imply that a compound binds one and only one target. Thus, a compound can and often does show specific binding of different strengths to several different targets and only nonspecific binding to other targets. Preferably, different degrees of specific binding can be distinguished from one another as can specific binding from nonspecific binding. Specific binding often involves an apparent association constant of $10^3$ $M^{-1}$ or higher. Specific binding can additionally or alternatively be defined as a binding strength (e.g., fluorescence intensity) more than three standard deviations greater than background represented by the mean binding strength of empty control areas in an array (i.e., having no compound, where any binding is nonspecific binding to the support). Most informative compounds have binding strengths within 1000-fold of three standard deviations of the background level. The range of affinities or avidities of compounds showing specific binding to a monoclonal or other sample can vary by 1-4 and often 2.5-3.5 orders of magnitude. An apparent association constant includes avidity effects (sometimes also known as cooperative binding) if present (in other words, if a target shows multivalent binding to multiple molecules of the same compound the apparent association constant is a value reflecting the aggregate binding of the multiple molecules of the same compound to the target). The theoretical maximum of the avidity is the product of the multiple individual dissociation constants, but in practice the avidity is usually a value between the association constant of individual bonds and the theoretical maximum. When contacted with a random selection of monoclonal antibodies, a subset of informative compounds (e.g., 1-20 or 5-15%) have association constants in the range of $10^3$ to $10^6 M^{-1}$ or $2 \times 10^3$ to $10^6 M^{-1}$ or $10^4$-$10^6 M^{-1}$ to at least one and sometimes several (e.g., at least 2, 5 or 10) different targets. A subset of all peptides or other compounds (e.g., at least 1%, at least 5% or 10%, 1-75%, 5-60%, 1-20% or 5-15% usually shows actual affinity constants of $10^3$-$10^6$ $M^{-1}$ to at least one and usually several targets (e.g., at least 2, 5 or 10). The same ranges of association constant apply to composite targets binding to the same compound in a complex sample. Of course different compounds in an array have different degrees of binding strength to components of a sample and some compounds can bind with higher or lower apparent association constants than these ranges.

Patients include humans, veterinary animals, such as cats, dogs, horses, farm animals, such as chickens, pigs, sheep, cattle and laboratory animals, such as rodents, e.g., mice and rats.

A binding profile of an array is a measure of the amount of component(s) of a sample bound to the different compounds of an array to a particular sample. The amount of component(s) bound reflects the amount of the components in the sample as well as the binding strength of components to the compounds. A binding profile can be represented for example as a matrix of binding strengths corresponding to the different compounds in an array. A binding profile typically includes binding strengths of a plurality of compounds (e.g., at least 2, 10, 50, 1000 or 1000 having association constants in a range of 1 mM to 1 µM to a sample or within a range of greater than but within a factor of 1000 of three standard deviations greater than the mean intensity of empty cells.

Binding strength can be measured by association constant, dissociation constant, dissociation rate, or association rate, or a composite measure of stickiness which may include one or more of these measures. The strength of a signal from a labeled component of a sample bound to immobilized compounds can provide a value for general stickiness. If a term used to define binding strength is referred to as "apparent" what is meant is a measured value without regard to multivalent bonding. For example, the measured value of an association constant under conditions of multivalent bonding includes a plurality of effects due to monovalent bonding among other factors. Unless otherwise specified binding strength can refer to any of these measures referred to above.

The term "nucleic acids" includes any and all forms of alternative nucleic acid containing modified bases, sugars, and backbones including peptide nucleic acids and aptamers, optionally, with stem loop structures.

The term "polypeptide" is used interchangeably with "peptide" and in its broadest sense to refer to a sequence of subunit natural amino acids, amino acid analogs including unnatural amino acids. Peptides include polymers of amino acids having the formula $H_2NCHRCOOH$ and/or analog amino acids having the formula $HRNCH_2COOH$. The subunits are linked by peptide bonds (i.e., amide bonds), except as noted. Often all subunits are connected by peptide bonds. The polypeptides may be naturally occurring, processed forms of naturally occurring polypeptides (such as by enzymatic digestion), chemically synthesized or recombinantly expressed. Preferably, the polypeptides are chemically synthesized using standard techniques. The polypeptides may comprise D-amino acids (which are resistant to L-amino acid-specific proteases), a combination of D- and L-amino acids, β amino acids, and various other "designer" amino acids (e.g., (β-methyl amino acids, Ca-methyl amino acids, and Nα-methyl amino acids) to convey special properties. Synthetic amino acids include ornithine for lysine, and norleucine for leucine or isoleucine. Hundreds of different amino acid analogs are commercially available from e.g., PepTech Corp., MA. In general, unnatural amino acids have the same basic chemical structure as a naturally occurring amino acid, i.e., an a carbon that is bound to a hydrogen, a carboxyl group, an amino group, and an R group.

In addition, polypeptides can have non-peptide bonds, such as N-methylated bonds (—N($CH_3$)—CO—), ester bonds (—C(R)H—C—O—O—C(R)—N—), ketomethylen bonds (—CO—$CH_2$—), aza bonds (—NH—N(R)—CO—), wherein R is any alkyl, e.g., methyl, carba bonds (—CH2-NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain. These modifications can occur at any of the bonds along the peptide chain and even at several (2-3) at the same time. For example, a peptide can include an ester bond. A polypeptide can also incorporate a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The compounds can also be peptoids (N-substituted glycines), in which the sidechains are appended to nitrogen atoms along the molecule's backbone, rather than to the α-carbons, as in amino acids.

The term "polysaccharide" means any polymer (homopolymer or heteropolymer) made of subunit monosaccharides, oligomers or modified monosaccharides. The linkages between sugars can include acetal linkages (glycosidic bonds), ester linkages (including phosphodiester linkages), amide linkages, and ether linkages.

DETAILED DESCRIPTION OF THE INVENTION

I. General

The invention provides arrays of compounds for use in profiling samples. The arrays include compounds binding to components of the samples at relatively low affinities. Although practice of the invention is not dependent on an understanding of mechanism, it is believed that under conditions of monovalent binding, different degrees of specific binding might be difficult to distinguish from each other and from nonspecific binding. However, the avidity of compounds binding to components of the samples can be increased by forming arrays such that components of the samples (e.g., antibodies or cells) can bind to more than one molecule of a compound at the same time. When a sample is applied to an array under such conditions, the compounds of the array bind to component(s) of the sample with significantly different affinities generating a profile characteristic of the sample. Such a profile usually includes some compounds having no specific binding to components of the sample and other compounds having different degrees of specific binding to components of the sample. Although such binding interactions are specific in the sense that overall binding profiles of an array are reproducible for replicates of the same sample and distinguishable between different samples, they are not necessarily unique in that compounds in the array usually show specific binding albeit of different degrees to a number of different components of a sample or different samples.

The avidity of informative compounds (i.e., those showing specific binding) in an array can be measured for monoclonal antibody samples. When measured against monoclonal antibodies selected from random (e.g., purchased from a commercial supplier as described in the Examples), informative compounds in some arrays often show apparent affinity association constants in a range of $10^4$-$10^9$, $10^6$-$10^9$, $10^4$-$10^7$, $10^4$-$10^6$ $M^{-1}$. Association constants of such informative compounds are often within a range of $10^3$-$10^6$ $M^{-1}$ or $10^4$-$10^5$ $M^{-1}$. When measured against a complex sample, similar ranges of apparent or actual association constants are observed; however, in this case, the constant are a composite of values for multiple different components within a sample binding to the same compound. Such affinities can be distinguished from nonspecific interactions. The proportion of informative compounds (i.e., compounds that show distinguishable binding among different targets) can vary depending on the composition of the array and the sample, but ranges of 1-75%, 5-60%, 1-20%, 5-15%, or 7-12% provide some guide. Given the data in Example 1 showing that different monoclonal antibodies have their own signature, it might have seemed impossible to meaningfully resolve patient samples which may contain $10^8$ or more different specificities of antibodies in the serum the array would be unresolveable. When an array is hybridized against a more complex sample, such as from a patient, the binding profile represents the aggregate effect of multiple components of a sample. Surprisingly despite the complexity of the samples, different samples are associated with different binding profiles. Also surprisingly, the intensity of binding profile often differs between patients with a disease or at risk of disease relative to normal patients. Relatively more compounds are informative for disease patients or patients at risk of disease relative to normals and binding intensities are relatively higher (e.g., biased toward the higher end of the range for a random selection of monoclonals) than for the nounal patients (intensities biased toward the lower end of the range for a random selection of monoclonals).

The binding profile of such an array to a sample can be used to characterize a sample. For example, the binding profile can be compared with binding profiles known to be associated with different diseases or stages of diseases or lack of diseases. Alternatively or additionally, the binding an be analyzed, for example, by using a compound binding relatively strongly to a component of the sample to affinity purify an antibody from the sample, or by comparing the sequence of a peptide in the array known to bind strongly to a component of a sample with a protein database to identify a protein in the sample. Remarkably, the same array can generate different and informative profiles with many different samples representing different disease states, disease stages, lack of disease and the like. Moreover, a profile characteristic of disease or departure from a nondisease state can be detected very early in development of a disease before typical analytical markers of disease would be detectable by conventional methods, such as ELISA.

II. Compounds for Use in Arrays

Many different classes of compounds or combinations of classes of compounds can be used for the arrays and methods of the invention. Classes of compounds include nucleic acids and their analogs, polypeptides (broadly defined as above), polysaccharides, organic compounds, inorganic compounds, polymers, lipids, and combinations thereof. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The test compounds can be natural or synthetic. The test compounds can comprise or consist of linear or branched heteropolymeric compounds based on any of a number of linkages or combinations of linkages (e.g., amide, ester, ether, thiol, radical additions, and metal coordination), dendritic structures, circular structures, cavity structures or other structures with multiple nearby sites of attachment that serve as scaffolds upon which specific additions are made. The compounds can be naturally occurring or nonnaturally occurring. Many different classes of compounds other than nucleic acids can be used, but optionally if the compounds are nucleic acids, the sample components detected are not nucleic acids. In some arrays, the test compounds have a molecular weight of between 500 and 10,000 Da, and optionally 1000 to 4000 Da.

The number of compounds is a balance between two factors. The more compounds, the more likely an array to include members having detectable affinity for any target of interest. However, a larger number of compounds also increases the cost of synthesizing and analyzing an array. Arrays typically have at least 100 compounds. Arrays having between 500 and 25000 compounds provide a good compromise between likelihood of obtaining compounds with detectable binding to any target of interest and ease of synthesis and analysis. Arrays having, for example, 100 to 50,000 members or 500-500,000, or 1000-25,000 members can also be used. However, arrays having much larger numbers of members for example, $10^2$-$10^7$ or 1000 to 5,000,000 or 500,000 to 2,000,000 can also be used. Such arrays typically represent only a very small proportion of total structural space, for example less than $10^{-6}$, $10^{-10}$, or $10^{-15}$ in the case of peptides. Sequence space means the total number of permutations of sequence of a given set of monomers. For example, for the set of 20 natural amino acids there are $20^n$ permutations, where n is the length of a peptide. Although it is widely assumed that most if not all of the residues in a peptide epitope participate in binding to the a target, it is much more likely that between two and five residues in a 10-12 mer epitope are involved in energetically favorable interactions with the target, the other residues are simply there to adjust the positions of the important residues, and to prevent inhibition of binding. Therefore, a relatively small number of peptides can provide a good representation of total sequence space, and include members capable of specific albeit low affinity interactions with a wide variety of targets. For example, 500-25,000 random peptides can cover evenly the entire shape space of an immune system ($10^7$ to $10^8$ antibodies in humans).

More compounds in the array should allow higher resolution of the diversity of compounds in the complex sample. For example, an array of 1 million compound would begin to approach the complexity of antibodies in a person's serum and therefore should allow more resolution of complex samples. Yet, even with a much smaller number of compounds, one is able to resolve new immune responses from infection or immunization.

For polymeric compounds, the lengths of polymers represent a compromise between binding affinity and ease of synthesis. There is some relationship between peptide length and binding affinity with increasing length increasing affinity. However, as peptide length increases the likelihood of binding a binding site on a target that interacts with the full peptide length decreases. Cost of synthesis also increases with increasing length as does the likelihood of insolubility. For peptide arrays, peptides having 8-35, 12-35, 15-25 or 9-20 residues are preferred. These ranges of monomer lengths can also be used for other polymers, although aptamers usually have longer lengths (e.g., up to 100 nucleotides).

The compounds (e.g., all or at least 80, 90 or 95%) are typically chosen without regard to the identity of a particular target or natural ligand(s) to the target. In other words, the composition of an array is typically not chosen because of a priori knowledge that particular compounds bind to a particular target or have significant sequence identity either with the target or known ligands thereto. A sequence identity between a peptide and a natural sequence (e.g., a target or ligand) is considered significant if at least 30% of the residues in the peptide are identical to corresponding residues in the natural sequence when maximally aligned as measured using a BLAST or BLAST 2.0 sequence comparison algorithm with default parameters described below, or by manual alignment and visual inspection (see, e.g., NCBI web site ncbi.nlm.nih.gov/BLAST or the like).

Some compounds are randomly selected from total sequence space or a portion thereof (e.g., peptides in which certain amino acids are absent or under-represented). Random selection can be completely random in which case any compound has an equal chance of being selected from sequence space or partially random in which case the selection involves random choices but is biased toward or against certain monomers, such as amino acids. Random selection of peptides can be made for example by a pseudorandom computer algorithm. The randomization process can be designed such that different amino acids are equally represented in the resulting peptides, or occur in proportions representing those in nature, or in any desired proportions. Often cysteine residues are omitted from library members with the possible exception of a terminal amino acid, which provides a point of attachment to a support. In some libraries, certain amino acids are held constant in all peptides. For example, in some libraries, the three C-terminal amino acids are glycine, serine and cysteine with cysteine being the final amino acid at the C-terminus. A library chosen by random selection, once selected is of known identity and can be reproduced without repeating the initial random selection process. Nevertheless, the compounds in such library retain the same random relations with one another. For example, the peptides in random library that is subsequently reproduced retain a random distribution throughout sequence space (with the possible exception of cysteine residues, if this residue is omitted). Collections of compounds, such as peptides, that are randomly distributed over sequence space, are still considered random even if reproduced without repeating the initial random selection.

The principles for selecting peptides and other compounds for arrays in the present methods are analogous to those for selecting initial libraries of compounds in producing synthetic antibodies, as further described in WO/2008/048970 and WO2009/140039.

III. Making Arrays

Compounds can be presynthesized and spotted onto a surface of an array or can be synthesized in situ on an array surface (see, e.g., Cretich et al., Biomol. Eng. 2, 77-88 (2006); Min et al., Current Opinion in Chemical Biology 8, 554-558 (2004), Breitling, Mol. BioSyst., 5, 224-234 (2009), U.S. Pat. No. 5,143,854; EP 476,014, Fodor et al., 1993, Nature 364, 555-556; U.S. Pat. No. 5,571,639, U.S. Pat. No. 5,593,839, EP 624,059, U.S. Pat. No. 6,620,584, EP 728,520). Customized arrays are also commercially available from suppliers such as Invitrogen or Pepscan. The surface is usually derivatized with a functional group that attaches to the compounds, optionally via linker. Compounds can be attached via covalent or noncovalent linkages. The array surface can be a single contiguous surface of a support. Alternatively an array can be formed by spotting or synthesizing different compounds on different particulate supports, such as beads. Peptides can be attached in either orientation (N or C) relative to the array. In general, the different compounds occupy different areas of a contiguous array or different particles in a particulate array. The identity of which compound occupies which area of an array or which particle is usually either known as a result of the synthesis process or determinable as a result of an encoding process. Encoding processes are commonly used for beads. The different areas in a contiguous array can be immediately adjoining as may arise when such arrays are the result of in situ synthesis, or separated, which is often the result of spotting.

An area or cell of an array is a unit of surface area from which a separate signal is detectable. In some arrays, each area of the array is occupied only by molecules of the same compound except for possibly a small degree of bleed over from one area to another, due for example, to imperfections in the array. In other arrays, some or all of the areas contain a pool of two or more different compounds. In such an array, the signal from an area containing a pool of two or more different compounds is the aggregate undivided signal from the compounds constituting the pool.

Such arrays typically contain from 100-5,000,000 compounds (e.g., 100-1,000,000, 500, 100,000 or 500-25,000 compounds) as discussed above. These numbers of compounds can readily be accommodated in different regions of an array of the order of 1-5 $cm^2$ combined area.

Within any one area of a contiguous array or within anyone particle of a particle array many different molecules of the same compound are present. Because compounds are usually attached to a derivatized surface of a support or particle (e.g., a support or particle bearing a linker), the density of molecules within an area of an array or a particle can be controlled in part by the derivatization process, for example, the period of time and concentration of derivatizing agent used. The density of molecules can also be controlled by the attachment or in situ synthesis process by which a compound is attached to a support. The length of a coupling cycle and concentration of compound used in coupling can both affect compound density.

The density of different molecules of a compound within an area of an array or on a particle controls the average spacing between molecules of a compound (or compounds in the case of a pooled array, which in turn determines whether a compound is able to form multivalent bonds with a multivalent binding partner in a sample. If two molecules of a compound or compounds in the case of a pooled array, are sufficiently proximate to one another, both molecules can bind to the same multivalent binding partner (for example to the two arms of an antibody). For peptides of length 15-25 residues an average (mean) spacing of less than 0.1-6 nm, 1-4 nm, 2-4 nm, e.g., 1, 2 or 3 nm is, for example, suitable to allow different regions of the same compound to undergo such multivalent bonding. Average (e.g., mean) spacings are typically less than 6 nm because spacings of 6 nm or more do not allow simultaneous binding of two sites on the same target. For example, for peptides of lengths 15-25 residues, the two identical binding sites of one antibody could not span more than 6 nm to contact two peptides at once. The optimum spacing for multivalent interactions may vary depending on the compounds used and the components of the sample being analyzed.

The formation of multivalent bonds can be shown by several methods. For example, the binding of an array to an interact antibody (i.e., two binding sites) can be compared with an otherwise identical antibody fragment (e.g., a Fab fragment) having only one binding site. Stronger binding to the intact antibody than the antibody fragment (e.g., higher apparent association constant) indicates multivalent binding. Multivalent binding can also be shown by comparing the binding of an array of an immobilized compound to an intact antibody with two binding sites with the reverse format in which the antibody is immobilized and the compound is in solution. Stronger binding (e.g., higher apparent association constant) of the immobilized compound to the antibody in solution compared with immobilized antibody to the compound in solution provides an indication that the immobilized compound can form multivalent bonds to the antibody. If capacity of compounds in array to form multivalent bonds in such a procedure is tested, it is usually sufficient to test one or a few sample compounds from the array for such binding. If the compounds in the array are of similar type, e.g., peptides of the same length, and deposited or synthesized under the same conditions, it can be inferred that if one or a few compounds on an array (e.g., 1-10%) are capable of multivalent binding, then so are the others. It is also not necessary to test every array that is made. Association (i.e., affinity) constants of compounds can be measured by conventional methods using technologies like SPR, ELISA, Luminex and other solution-phase binding (e.g., monitoring changes in bound signal over time) when the antibody or other sample is immobilized and the compound is in solution. Conversely, apparent association constants can be measured when a compound is immobilized and antibody or other sample is in solution. Once suitable synthesis or deposit conditions have been established for achieving arrays capable of multivalent binding, other arrays can by made under the same conditions without individualized testing.

Usually, different compounds are deposited or synthesized in different areas of an array under the same conditions, so that if one compound is spaced so that it is capable of multivalent binding, most or all compounds are. In some arrays, at least 10%, 50%, 75%, 90% or 100% of compounds in the array are spaced so as to permit multivalent binding with a multivalent binding partner. However, it is not necessary that all compounds be deposited or synthesized with the same spacing of molecules within an area of the array. For example, in some arrays, some compounds are spaced further apart so as not to permit or permit only reduced multivalent binding compared with other compounds in an array.

The spacing can be measured experimentally under given conditions of deposition by depositing fluorescently labeled compounds and counting photons emitted from an area of an array. The number of photons can be related to the number of molecules of fluorescein in such an area and in turn the number of molecules of compound bearing the label (see, e.g., U.S. Pat. No. 5,143,854). Alternatively, the spacing can be determined by calculation taking into account the number of molecules deposited within an area of an array, coupling efficiency and maximum density of functional groups, if any, to which compounds are being attached. The spacing can also be determined by electron microscopy of an array.

Arrays having larger spacing that do not permit multivalent interactions or do so to a reduced extent compared with spacing described above also have application in identifying high affinity interactions. This type of strategy can be used to identify peptides or other compounds, for example, that are very close structurally to the original epitope that raised the antibody response. Alternatively, for arrays of peptides from life space, this spacing facilitates identifying the true epitope.

The spacing between compounds can also be controlled using spaced arrays; that is, arrays on surfaces coated with nano-structures that result in more uniform spacing between compounds in an array. For example, NSB Postech amine slides coated with trillions of NanoCone apexes functionalized with primary amino groups spaced at 3-4 nm for a density of 0.05-0.06 per $nm^2$ can be used.

Array formats that can be used include microarrays, beads, columns, dipsticks optical fibers, nitrocellulose, nylon, glass, quartz, mica, diazotized membranes (paper or nylon), silicones, polyformaldehyde, cellulose, cellulose acetate, paper, ceramics, metals, metalloids, semiconductive materials, quantum dots, coated beads, other chromatographic materials, magnetic particles; plastics and other organic polymers such as polyethylene, polypropylene, and polystyrene; conducting polymers such as polypyrrole and polyindole; micro or nanostructured surfaces, nanotube, nanowire, or nanoparticulate decorated surfaces; or porous surfaces or gels such as methacrylates, acrylamides, sugar polymers, cellulose, silicates, and other fibrous or stranded polymers.

An exemplary method of array preparation is as follows. A microarray is prepared by robotically spotting distinct polypeptides on a glass slide having an aminosilane functionalized surface. Each polypeptide has a C-terminal glycine-serine-cysteine as the three C-terminal residues and the remaining (17) residues determined by a pseudorandom computational process in which each of the 20 naturally occurring amino acids except cysteine had an equal probability of being chosen at each position. Polypeptides are conjugated to the aminosilane surface by thiol attachment of the C-terminal cysteine of the polypeptide to a maleimide (sulfo-SMCC, sulfosuccinimidyl 4-[N-maleimidomethyl]cyclohexane-1-carboxylate which is covalently bonded to the aminosilane surface. The polypeptides are chemically synthesized, dissolved in dimethyl formamide at a concentration that may range from about 0.1 mg/ml to about 2 mg/ml, and then diluted 4:1 with phosphate-buffered saline prior to spotting. The concentration of peptide or other compound determines the average spacing between peptide molecules within a region of the array. A concentration of 1 mg/ml gives an average spacing of about 0.5 nm. The spacing decreases non-linearly with dilution at lower concentrations. The printed slides stored under an argon atmosphere at 4° C. until use.

An exemplary calculation of spacing is as follows: spot size: 150 μm, spot area: 17671 $μm^2$, nanoprint deposition volume: 200 pL, peptide concentration: 1 mg/ml, deposition amount: 200 pg, # peptides deposited: $8 \times 10^{10}$ per spot, $8 \times 10^{10}$ peptides/17671 $μm^2 = 4.5 \times 10^6$ peptides/$μm^2$, $2.2 \times 10^{-7}$ $um^2$ area needed by 1 peptide ($4.6 \times 10^{-4}$ μm spacing).

As well as including compounds randomly or without regard to the sample being analyzed, arrays can include other compounds known to bind particular targets, such as proteins, in a sample. These compounds can be antibodies, synbodies or peptides among others. Usually, such interactions are high affinity (e.g., greater than $10^7$, $10^8$ or $10^9$ $M^{-1}$). The number of such known binding partner compounds can be large, for example, there can be a different compound for at least 25, 50, 75, or 90% or substantially all of the known proteins expressed by a given genome, such as the human genome). The different known binding partner compounds occupy different areas of the array in similar fashion to randomly selected compounds. However, because the known binding partner compounds are in general capable of high affinity interactions, they can be used with or without an intermolecular spacing that permits multivalent interactions with the sample. Although one might think that inclusion of compounds selected at random or without regard to the sample being analyzed would be redundant in view of inclusion of known binding proteins to a large part or all of the encoded proteins in a genome, such is not the case because some diagnostic immune responses are the result of somatic mutation or non-protein components and not detected by binding proteins to encoded proteins.

IV. Samples and Components to be Analyzed

The arrays and methods of the invention can be used for analyzing any kind of sample containing or potentially containing analyte(s) of interest. Of particular interest are samples from human or veterinary patients or laboratory model animals. Such samples can be blood (including whole blood, red cells, plasma and the like), urine, feces, saliva, CNS fluid, other body fluids, hair, skin, biopsies and the like. A profile can be obtained from a small volume of sample, e.g., ≤1 µl. Some samples are from patients known or suspected to be suffering from a disease. The identity of the disease may or may not be known. Some samples are obtained from patients known to have been subjected to a risk of disease but in which symptoms of disease are not yet evident. The risk can be genetic (e.g., a particular gene or family history) or experiential (e.g., exposure to a toxic chemical or radiation). Samples can also be obtained from patients who have been vaccinated to analyze the resulting immune response.

Samples from patients can include a wide variety of components subject to potential analysis by an array. The components most amenable to detection are those capable of multivalent bonding to compounds in the array. Such components include antibodies, which can support multivalent bonding through their pairs of heavy and light chains (i.e., two binding sites per antibody) and cells, which can form multiple bonds through multiple copies of receptors displayed from their outer surfaces. Viruses can also form multivalent bonds through different copies of coat proteins on their outer surface. Samples from patients can include many different antibodies and/or different cells and/or other components.

Samples can be analyzed with little if any further processing or can be subject to further processing such that only selected components of the sample (e.g., antibodies or cells) are analyzed with the array.

V. Methods of Detection

Binding interactions between components of a sample and an array can be detected in a variety of formats. In some formats, components of the samples are labeled. The label can be a radioisotype or dye among others. The label can be supplied either by administering the label to a patient before obtaining a sample or by linking the label to the sample or selective component(s) thereof.

Binding interactions can also be detected using a secondary detection reagent, such as an antibody. For example, binding of antibodies in a sample to an array can be detected using a secondary antibody specific for the isotype of an antibody (e.g., IgG (including any of the subtypes, such as IgG1, IgG2, IgG3 and IgG4), IgA, IgM). The secondary antibody is usually labeled and can bind to all antibodies in the sample being analyzed of a particular isotype. Different secondary antibodies can be used having different isotype specificities. Although there is often substantial overlap in compounds bound by antibodies of different isotypes in the same sample, there are also differences in profile.

Binding interactions can also be detected using label-free methods, such as surface plasmon resonance (SPR) and mass spectrometry. SPR can provide a measure of dissociation constants, and dissociation rates. The A-100 Biocore/GE instrument, for example, is suitable for this type of analysis. FLEXchips can be used to analyze up to 400 binding reactions on the same support.

Optionally, binding interactions between component(s) of a sample and the array can be detected in a competition format. A difference in the binding profile of an array to a sample in the presence versus absence of a competitive inhibitor of binding can be useful in characterizing the sample. The competitive inhibitor can be for example, a known protein associated with a disease condition, such as pathogen or antibody to a pathogen. A reduction in binding of member(s) of the array to a sample in the presence of such a competitor provides an indication that the pathogen is present.

The stringency can be adjusted by varying the salts, ionic strength, organic solvent content and temperature at which library members are contacted with the target.

VI. Applications

The arrays have a wide variety of applications in analyzing or characterizing clinical, veterinary, forensic, laboratory and other samples. As with conventional diagnostics, the arrays can be used to identify particular analytes within samples, for example, analytes associated with particular disease. However, the methods can also be used to provide a binding profile of different compounds characterizing a sample. The binding profile represents the aggregate interactions of the compounds with different components in the sample, and can be characteristic of a particular disease, stage of disease or lack of disease. The different components can be complex (e.g., at least 10, 100, 1000 or 1,000,000 different antibodies and/or different cells).

A binding profile typically includes compounds whose interactions with the sample are nonspecific as well as compounds whose interaction with the sample reflect specific but low affinity interactions (i.e., apparent or actual dissociation constant between 1 mM and 1 µM). Compounds with higher affinity interactions (i.e., dissociation constant less than 1 µM) may or may not be present. Such higher affinity interactions if present may arise by chance as a result of a compound in the array being a mimetic of a natural binding partner of a sample component or as a result of including a control in which a compound is a known binding partner of a component of a sample. However, a sample can usually be adequately characterized by the binding profile of compounds with low affinity interactions with the sample, optionally in combination with compounds lacking specific binding to components of the sample. For example, the identity and relative binding of at least 2, 5, 10 or 50 compounds capable of low affinity specific binding to components of the sample can often be used to characterize the sample. Such low affinities actions may in part be the result of compounds serving as mimetopes providing a linear epitope that (imperfectly) resemble an epitope against which an antibody in the same was raised (e.g., a complex 3D-structure).

One application lies in analyzing samples from patients known or suspected to be suffering from a disease but in which the particular disease affecting the patient is not known. A conventional approach would be to perform separate assays for suspected diseases. By contrast, in the present methods, a single binding profile from the patient sample can be used to characterize the patient for many diseases, stage of disease or lack of disease. The binding profile can be used to characterize the sample for virtually any disease, including autoimmune disease, cancer, infectious diseases, and diseases of the CNS. Most if not all diseases involve some changes in antibodies, cells or other components present in patient samples, reflected in a binding profile. Some exemplary infectious diseases include bacterial, fungal and viral diseases, such as Valley Fever, Q-fever, *Tularemia tularensis*, *Rickettsia rickettsii*, HSV types I and II, HVB, HVC, CMV, Epstein Barr virus, JC virus, influenza, A, B or C, adenovirus, and HIV. Because different infections give different profiles, different infections in a patient having multiple infections can be detected simultaneously. Some exemplary cancers that can be diagnosed or prognosed using the methods of the invention include glioblastoma, breast cancer, multiple independent primary cancer and/or recurrence situation, pancreatic cancer, lung cancer, myeloma, ovarian cancer and esophageal cancer. Precancerous cells that are morphological distinguishable from normal cells but not yet cancerous can also be detected using the methods of the invention. Neurological diseases, such Alzheimer's disease, although not generally considered to be an autoimmune disease, results in some changes in antibodies present in a sample. The same is the case for chronic diseases, such as Asthma, Rheumatoid arthritis, Diabetes mellitus type 1, Psoriasis, Multiple Sclerosis and others.

Another application lies in analyzing samples from patients known or suspected to have a particular disease, but in which the stage, severity or prognosis for the disease is unclear. Again the binding profile can provide an indication of any of these factors.

Another application lies in analyzing samples from vaccinated patients to determine whether an adequate protective immune response is developing. The pattern of response in one patient can be compared, for example, with a patient who has been naturally infected with the pathogen and survived, a similarity of response pattern indicating the patient is likely to survive and a dissimilarity that the patient will get worse or die at least in the absence of alternate treatment. Alternatively, a profile of a patient or animal model immunized with a new vaccine (for example in a clinical or preclinical trial) can be compared with profiles of patients or control animals immunized with an existing vaccine known to be effective. In a further variation, patients being recruited for a clinical trial of a vaccine can be prescreened for binding profile. Those already having a binding profile similar to that of a patient immunized with a vaccine known to be effective or from a patient who has survived a natural infection can be eliminated from the trial because their inclusion might lead to a misleading placebo response.

Another application lies in screening samples from patients who have undergone organ transplant (particularly allotransplantation). The profile in a patient under test can be compared with profiles of patients undergoing organ transplant who have or have not undergone rejection following the transplant. Similarity of the profile between a patient under test and a patient who has previously undergone rejection (or an average profile of a collection of such patients) indicates that the patient is at risk or is undergoing rejection.

Another application lies in analyzing samples from a patient known to be at risk of a disease but in which symptoms of disease are not yet present. The risk can be genetic, such as a genetic mutation associated with disease or family history of the disease, or arise as a result of experience, for example, exposure to a toxic chemical, radiation, traumatic accident, stress, fatigue, chemotherapy, unprotected sex, or exposure to a subject with a contagious disease. Such a patient is naturally concerned about the possibility of acquiring a disease and early therapeutic intervention. The methods are particularly useful in crisis situations in which many subjects have had potential exposure to a risk. Conventional diagnostic assays often have a significant lag period before a disease can be developed. For example, conventional viral assays can take several months to develop detectable patient antibodies. Autoimmune diseases (e.g., lupus, type 1 diabetes, rheumatoid arthritis, multiple sclerosis) can take several years to develop specific autoantibody or T-cell responses to specific autoantigens. By contrast, the present methods can detect changes in a profile within a few days (e.g., less than 10, 5 or 3 days) of exposure to a risk, or infection. The changes in binding profile may reflect subtle changes in concentrations of many different components of a sample, few if any of which would be individually detectable. However, in the aggregate, the changes in binding profile of the compounds in the array indicate a change if the risk has started development of disease.

Another application lies in forensic analysis of a sample, for example, a sample recovered from a crime scene or a sample relevant to a paternity analysis. Comparison of a test sample with one or more references samples of known origin can provide an indication of the source of the test sample.

Binding profiles can be used in a variety of ways in characterizing a sample. In some methods, a binding profile of a sample is compared with one or more reference binding profiles of the same compounds. A reference binding profile is a profile that characterizes a particular disease, stage of disease or lack of disease, and the like. Reference profiles are typically determined by averaging binding profiles of several samples (e.g., at least 2, 20, 50 or 100) each characterized for the same disease, stage of disease or lack of disease.

Comparison of a sample binding profile with a reference binding profile can involve comparing the different binding strengths of different compounds in an array to the respective samples to derive a value representing the overall similarity of the profiles. A measure of similarity on a scale of similarity is by implication an inverse measure of dissimilarity and vice versa. Thus, a value representing the overall similarity includes a value representing the overall dissimilarity. However, mathematically dissimilarity matrices can be handled and analyzed distinctly from similarity matrices. Raw data from the sample being analyzed can of course be normalized before the comparison to eliminate any differences due to sample size, processing, concentration and the like, rather than relative representation of sample components. Standard ANOVA analyses can also block such nuisance factors, provided such factors are accounted for in the experimental design.

Various techniques can be used to derive a value based upon the comparison of a binding profile and a reference binding profile. A derived value can be used to measure the dissimilarity between the binding profile and the reference profile and be evaluated using a distance measure such as the Euclidean Distance (ED) metric. The ED metric is typically used for measuring the distance between two vectors of "n" elements. According to one implementation, if x=(x1, x2, x3, ..., xN) and y=(y1, y2, y3, ..., yN) are two points in Euclidean N-space, then the Euclidean distance between x and j may be computed as:

$$D_{xj} = \text{SquareRoot}(\text{Summation}((x_i - y_i)^2))$$

The ED metric thus not a correlation (0 to 1), but a measurement of dissimilarity.

In the context of comparing a binding profile (defined by its binding values for each point in N-dimensional space, where N is the number of experimental points (conditions)) with a reference binding profile, a ED metric can be determined regardless of the complexity, number of peptides, or number of patients. Each profile being compared may be seen as a pattern: setting an explicit series of points across time, across dilutions, across disease states, across symptoms, etc., and the comparison described here looks for data that reflects this defined series of points.

To standardize the difference between binding profiles being compared, the calculated ED measurement may be normalized by dividing by the square root of the number of conditions as follows:

$$\text{Distance} = |a - b| / \text{square root of } N$$

This is distinct from the aforementioned distance calculation by normalizing for the total number of conditions. This prevents the distance calculation from expanding too far given large numbers of samples.

Accordingly, calculating the Euclidean distance between two data points involves computing the square root of the sum of the squares of the differences between corresponding values. Because the ED metric is a measure of dissimilarity, the distance (d) may be converted, when needed, to a similarity measure as $1/(1+d)$. Distance, similarity, and dissimilarity are interchangeable to a certain degree but each is a uniquely useful given the calculations being applied. As the distance gets larger, the similarity gets smaller. This renders the original data useful for looking at differences in a non-biased and geometrical way. The computation is scalable with increasing number of experiments. In fact, the complexity of the pattern is inherently diminished to the calculation because it is in the denominator and is a square root.

Other distance metrics that can be used include Euclidean Squared, Pearson Correlation, Pearson Squared, Spearman Confidence or Correlation, and other like techniques.

Binding profiles can also be used in various analytical methods to further characterize the sample. For example, a compound in the array showing relatively strong binding to the sample (compared with other compounds in the array) can be used to affinity purify a component of the sample. The component can then be further characterized (e.g., by sequencing or immunoreactivity). The identity of the compound may be characteristic of a disease state (e.g., a pathogen, autoantibody or tumor associated antigen). If the component is not already known to be characteristic of a disease state, it can be used as a new target for developing therapies or diagnostics against the disease state. For example, autoantigens or peptides thereof, can be used in inducing tolerance of autoimmune disease. Alternatively, after washing off unbound cellular components, the cellular components binding to an array can be dissociated from the array, fractionated and analyzed in similar fashion. In a further variation, the identity of a compound in the array showing relatively strong binding to a sample can be used to identify a ligand of the component bound in the sample, and hence the component in the sample. For example, if the compounds of the array are peptides, the sequence of a peptide showing relatively strong binding to a sample can be compared with a database of protein sequences. Comparison can be pairwise between a database sequence and a peptide in the array or between a database sequence and a motif or consensus sequence from a plurality of peptides in the array. Sequence similarity to a protein in the database provides an indication that the protein is a ligand of the component in the sample to which the peptide showed strong binding. The identity of a ligand in turn provides at least an indication of potential molecules in the sample and in turn disease states characterized by such molecules.

The same array can be used in any of the applications described above and for virtually any disease or suspected disease state. The same array means either literally the same array, in which case the array may be washed between different samples, or different copies of an array of the same composition. The identity of which compounds in the array are most informative for a disease or other state being analyzed varies by state. Thus, having identified the most informative compounds for a particular disease, derivative arrays or other detection devices and kits can be made that have a reduced number of compounds including the most informative compounds. The derivative arrays are sometimes referred to as secondary arrays to distinguish them from primary arrays used in initial identification of binding compounds and sometimes a sample component bound by these compounds.

A further useful aspect of the present methods is that they can detect not only increased binding of compounds to cellular components in test samples relative to a control sample representing an undiseased subject (typically a human) but can also detect decreases. For example, some sample components, particularly antibodies, can be detected to decrease in a test sample, such as a disease or vaccinated sample or any other of the samples types mentioned, and other sample components increase.

VI. Derivative Analyses

As well as being useful in themselves for analyses of samples as discussed above, the present methods are also useful for determining derivative compounds and detection devices. In a simple form of such methods, a derivative device or other array in constructed containing one or more compounds known to be associated with a given disease, susceptibility to disease or other condition described above, and omission of other compounds from the primary array not found to be informative for this disease, susceptibility or other condition. In some such methods, only a small proportion of the compounds used in a primary array (e.g., less than 0.1%, 1% or 5% are retained). In other methods, a component of the sample bound by some of the compounds in a primary array is identified by any of the approaches discussed in the previous section. Having identified a component of the sample, one or more known binding partners of the component are also identified. The known binding partners can be compounds from the primary array, antibodies to the component or other compound, such as a synbody that is known to bind to the component. The known binding partner(s) can then be used to detect the sample component to which they are known to being by any otherwise conventional diagnostic assay. For example, if the known binding partner is an antibody, the assay can be an ELISA, immunoprecipitation, radioimmunoassay or the like. If a plurality of known binding partners are used, the known binding partners can be immobilized in an array format. The known binding partners can also be incorporated into diagnostic kits or diagnostic device (e.g., attached to a support). Such arrays, diagnostic devices and kits can be manufactured by conventional means. Of course, once the known binding partners of a component have been identified, it is not necessary to repeat the initial screening with the primary array for subsequent manufacture of such arrays, diagnostic devices and kits.

Although the invention has been described with reference to the presently preferred embodiments, various modifications can be made without departing from the invention. Unless otherwise apparent from the context any step, element, embodiment, feature or aspect of the invention can be used with any other. All publications (including GenBank Accession numbers and the like), patents and patent applications cited are herein incorporated by reference in their entirety for all purposes to the same extent as if each individual publication, patent and patent application was specifically and individually indicated to be incorporated by reference in its entirety for all purposes. If more than one version of a sequence is associated with a deposit number at different times, the version associated with the deposit number at the effective time of filing the application is meant. The effective time of filing means the earliest application from which priority is claimed disclosing the relevant accession number.

EXAMPLES

Example 1

Array Binding to Monoclonals

Figure 12:
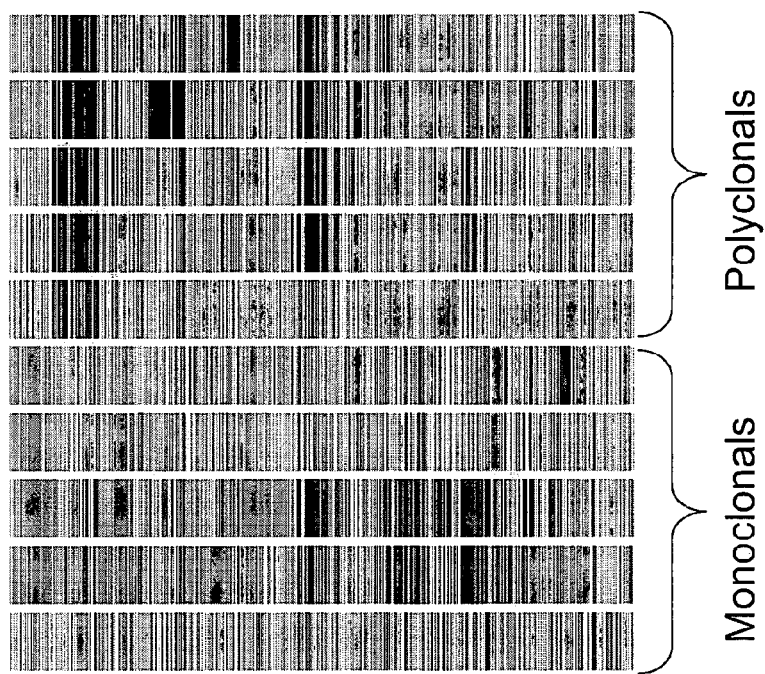
FIG. 12 compares the binding profile of several monoclonal and polyclonal antibodies to different peptides in an array.

Triplicate copies of an array having 10,000 different random peptides made by robotically spotting distinct polypeptides on a glass slide having an aminosilane functionalized surface as described above were tested for binding to individual antibodies were hybridized at 100 nM, 37° C., 8 rpm, 1 hour and detected with 5 nM secondary antibody. The antibodies tested included; (1) monoclonals, (2) polyclonals, (3) unknown epitope, (4) monoclonals with linear epitopes, (5) monoclonals with discontinuous epitopes, (6) anti-Fc antibodies, (7) polyreactive antibodies, (8) autoantibodies, (9) mixed monclonals, and (10) antibodies to glycans. Triplicate arrays were mathematically averaged, and the most informative 800 peptides were used to distinguish the relative differences. The binding of each antibody or antibody mixtures to the 800 peptides can be represented by a series of colored bands as shown in the right of FIG. 1. Each band represents binding to a different one of the 800 informative peptides in the array. Different colors can be used to represent the different strengths of binding, for example, red being the highest, blue the lowest and yellow intermediate. The apparent binding affinities of most of the informative peptides to the antibodies tested range from about $10^4 \text{ M}^{-1}$ to $10^6 \text{ M}^{-1}$ or 100 (background, e.g., an empty cell of an array lacking a peptide) to 65,500 in intensity unity. The left portion of FIG. 1 shows principal component analysis of the patterns shown in the right hand proportion of a figure. Principal component analysis represents the binding profiles of different antibodies as spots on a two-dimensional chart, such that the relative distance between the spots is a measure of the relatedness of patterns. The principal component analysis shows that each of the antibodies has a distinguishable binding profile. The analysis also shows that technical replicates are very reproducible per array and per peptide. The distinct binding patterns of different monoclonal and polyclonal antibodies are also shown in FIG. 12.

Figure 11:
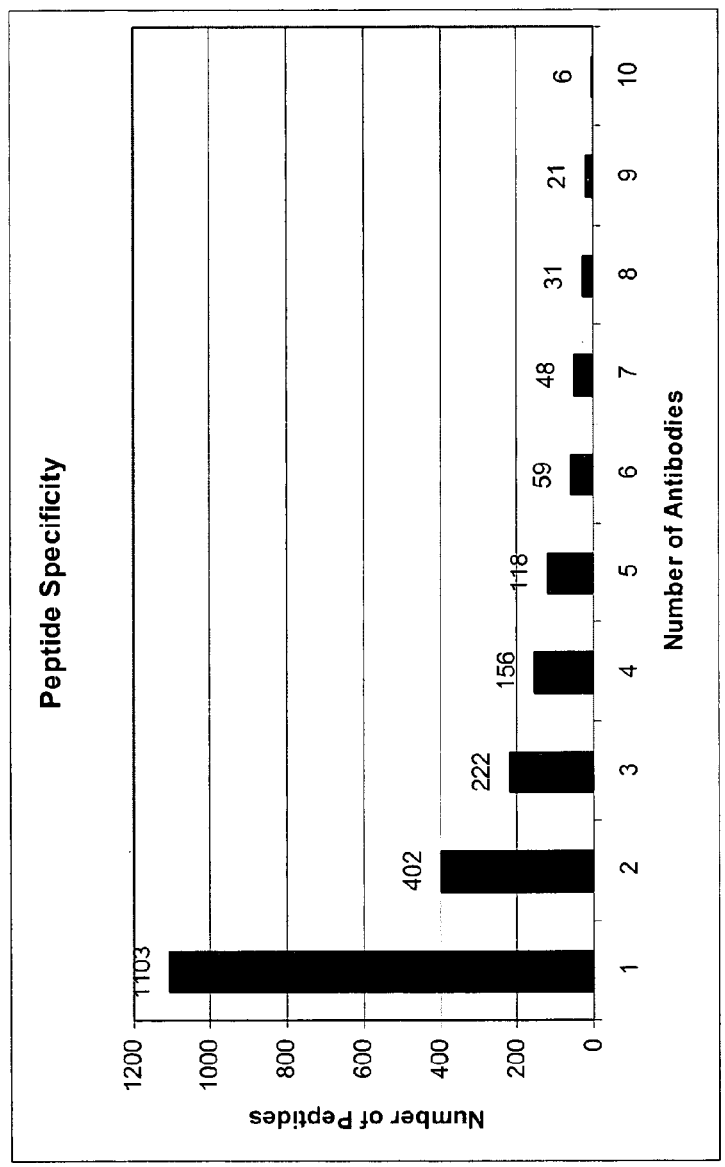
FIG. 11 shows an analyses of the number of different peptides binding to different numbers of antibodies.

FIG. 11 shows an analyses of the number of different peptides binding to different numbers of antibodies. For example 1103 peptide bound to one and only one of the antibodies tested. 402 peptides bound to two of the antibodies tested. Six peptides bound to ten different antibodies and so forth. Thus, the different peptides have different degrees of promiscuity in binding to multiple targets. Such a range of promiscuities can be of assistance in using an array to characterized multiple samples.

Of over twenty types of monoclonal antibodies, each produced a distinct pattern on the array. These differences included both what peptides bind and the relative binding to each. Signals on the array varied over 3 logs of fluorescence intensity. The results show antibodies against sugars, non-natural protein sequences (e.g. frameshift peptides, translocation junctions, splice variants), self-proteins, post-translational modifications (PTM's), multi-species, and multi-class (IgG, IgA, IgM, IgE) are all detected. Because each antibody has a distinct pattern of binding, one might expect that the $10^8$ repertoire of serum antibodies would create a monotonic pattern indistinguishable between different samples. Indeed a mathematical reconstruction of the binding of 30 monoclonals indicates that the distinctive patterns start to be lost. Remarkably as shown in subsequent examples, this is not the case in reality.

Example 2

Dilution

Figure 2:
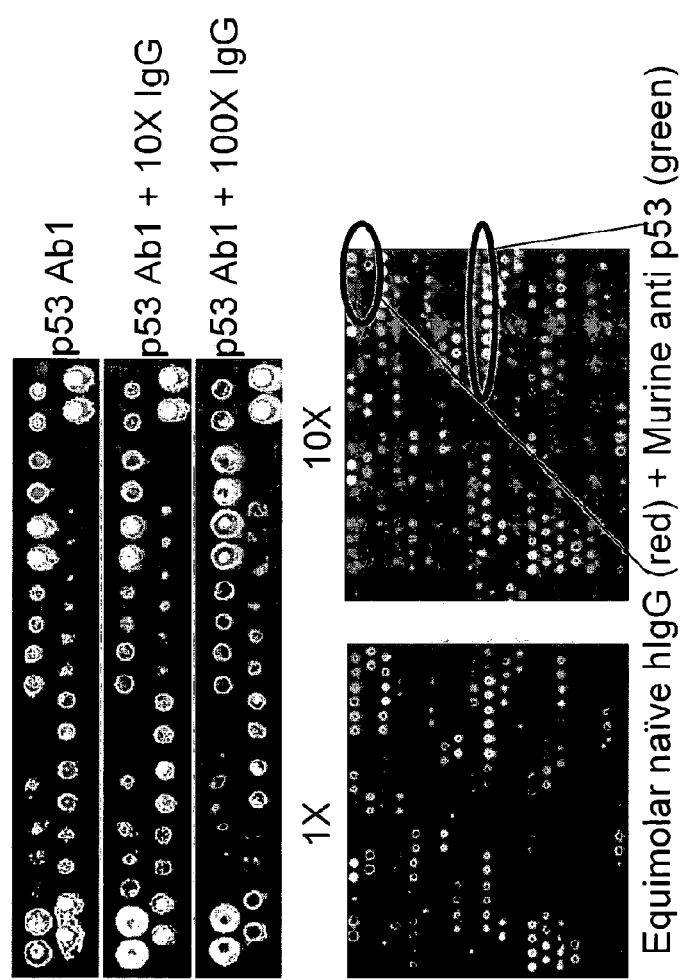
FIG. 2 shows the signal from peptides that bind to monoclonal antibodies in the presence or absence of competitor.

A single monoclonal antibody, p53Ab1, was used to test the ability to discern a signature or binding profile in the presence of competing IgG. As before, 100 nM p53Ab1 was hybridized to the arrays to detect its signature. We added 1, 10, and 100-fold pooled human IgG as competitor and could still distinguish the original signal. For the 2-color experiments, IgG was detected with a red fluor, p53 with a green fluor and the competing spots were detected by multi-wavelength scanning FIG. 2 shows the signal from the most informative peptides in the different conditions tested. The signal from the monoclonal stands out against the complex background of the IgG serum. This is a key and unexpected aspect of the immunosignaturing technique. High affinity immune responses, like monoclonals mixed in serum, stand out on the arrays from the normal antibodies.

Figure 3:
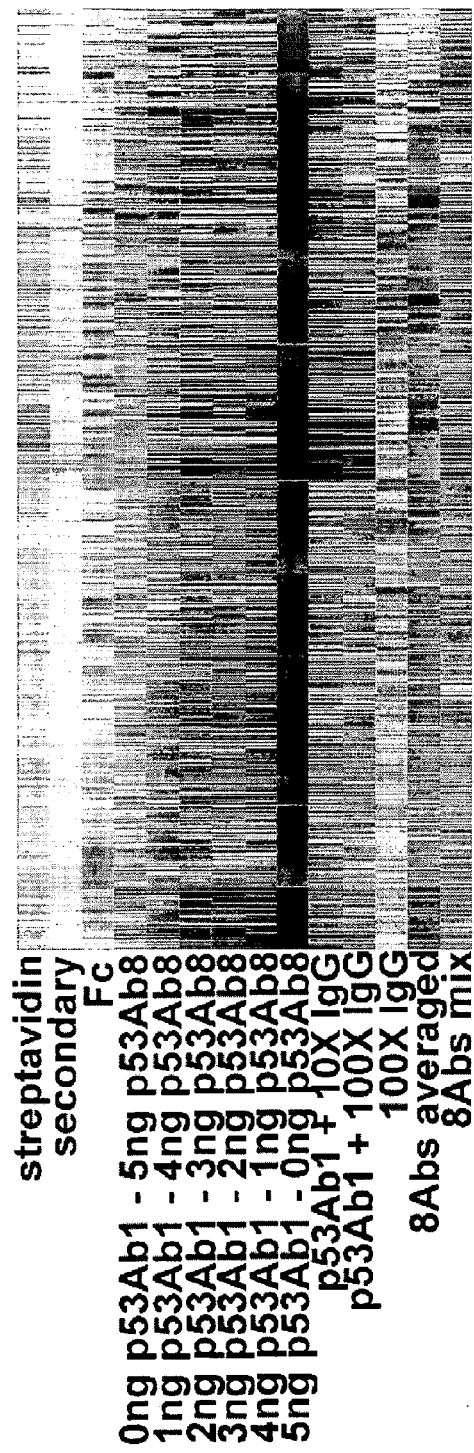
FIG. 3 shows the binding intensities to the 300 most informative peptides that distinguish mixtures of two different monoclonal antibodies with and without competitor. Different levels of white to black indicate strength of binding of peptide to antibody.

Two antibodies were selected against p53, Ab1 and Ab8. Each was titrated into the other yielding a gradient of signatures. FIG. 3 shows the binding intensities to the most informative peptides in which different colors are used to represent different binding strengths. As seen the strongest pattern, Ab8, is seen in the presence of another antibody and in the presence of competing IgG. Eight antibodies mixed together show a trend towards monotonic response. 100× IgG shows exactly this. Dilution shows that pattern of p53Ab1 dominates a poorer antibody, p53Ab8 and excess IgG. Physically pooled antibodies and antibody signals mathematically averaged show similar patterns. Secondaries and tertiaries were not detectable.

Example 3

Resolving Disease

Figure 4:
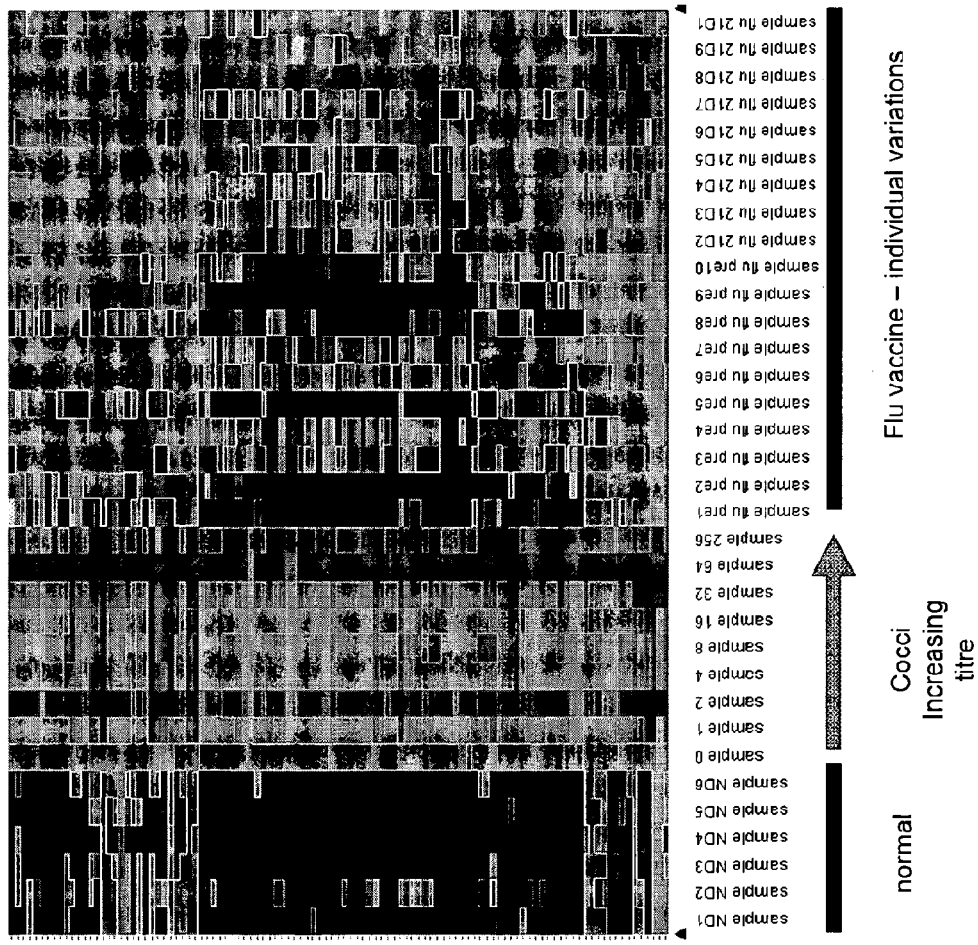
FIG. 4 shows the binding profiles of patients with either Valley Fever, Influenza, Influenza Vaccine recipients, of healthy volunteers indicating the distinct pattern of binding specific to a disease for the 100 informative peptides shown.

We collected normal donor sera and sera from patients infected with Valley Fever and Influenza vaccine recipients. Valley Fever patients were previously typed against CF antigen for titer. FIG. 4 shows the binding profiles of different patients for the most informative patients with different color bands representing different binding intensities. In general, normal undiseased patients, showed a low intensity pattern. Patients infected with cocci showed a much higher intensity pattern even when no titer of cocci could be detected. Patients inoculated with flu vaccine showed varying patterns likely corresponding to the strength of the immune response. These patterns were readily distinguishable from the normal patients and cocci infected patients.

Figure 5:
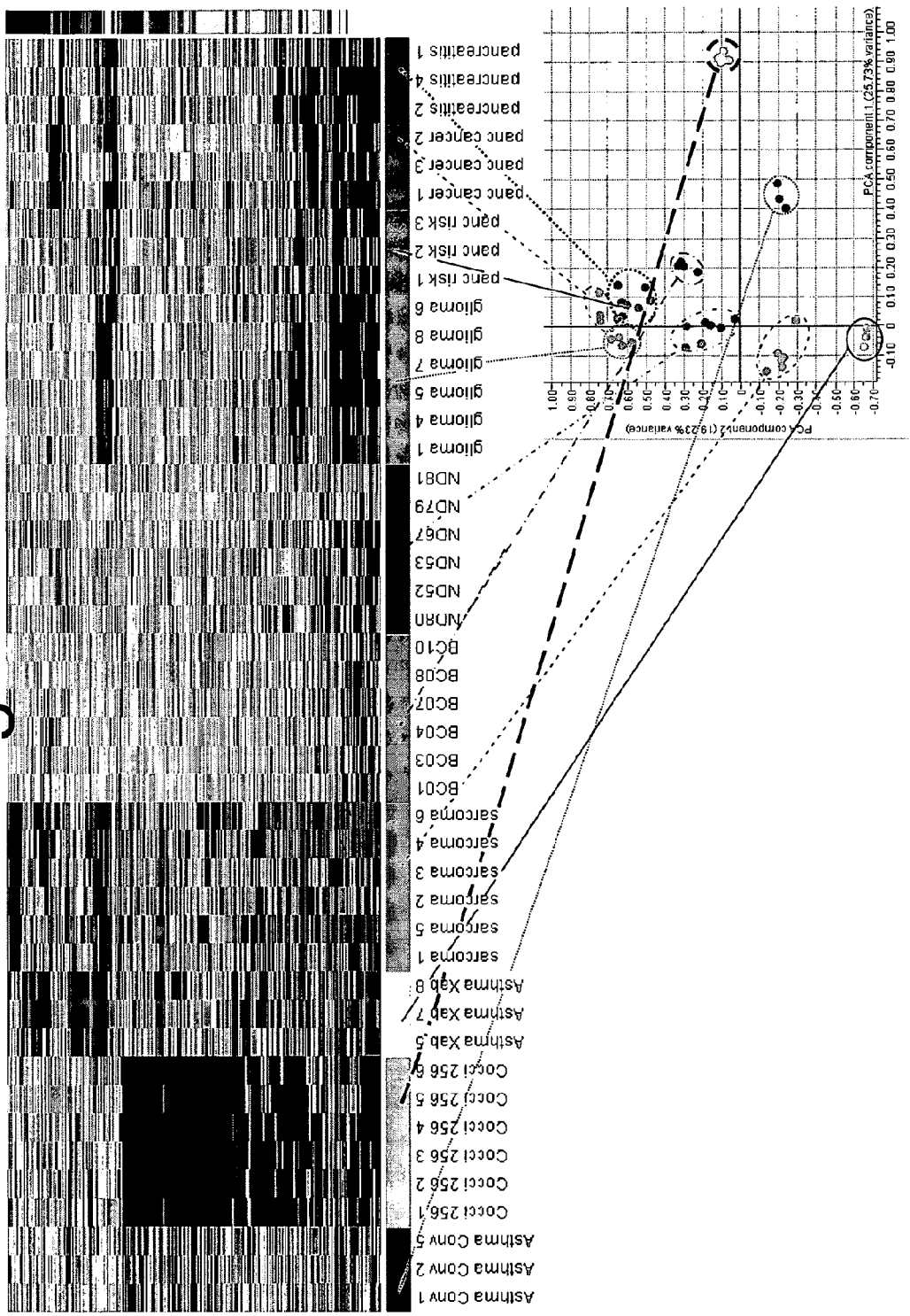
FIG. 5 shows the binding profile of the 88 most informative peptides that distinguish Asthma, Valley Fever (Cocci), Sarcoma, Breast Cancer, Glioma, Pancreatic Cancer, Pancreatitis, and healthy volunteers. The lower panel shows the principal components map for the same peptides and provides a view of the degree of separation between samples (in 2 dimensions).

In a further experiment, samples from about 200 cancer patients having various kinds of cancer including glioma, sarcoma and pancreatic cancer were tested. FIG. 5 shows the binding profile of the most informative peptides in comparison with cocci infected patients and asthma patients. Principal component analysis confirms that the patterns of patients with these different diseases are distinct, and the patterns of cancer patients show clustering by the type of cancer.

Figure 6:
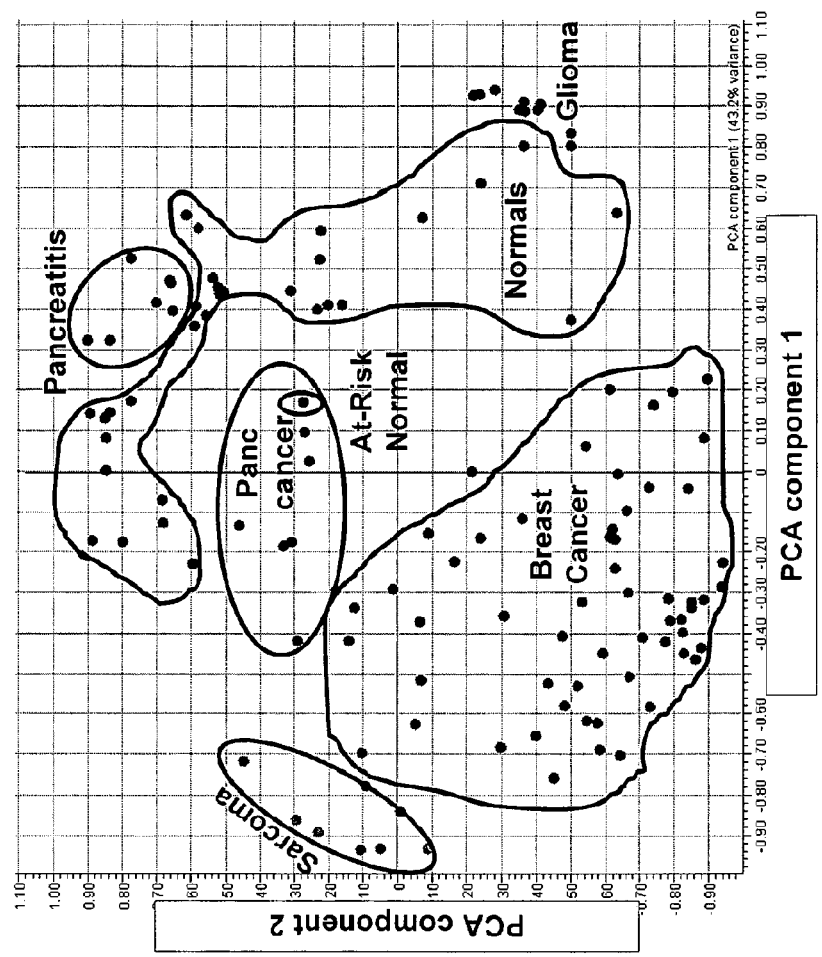
FIG. 6 shows principal component analysis of patients having or at risk of pancreatic cancer in the context of other diseases (Breast Cancer, Sarcoma, Pancreatitis, Glioma).

In a further experiment, samples from patients at risk of pancreatic cancer and/or having pancreatitis were compared with patients having pancreatic cancer, patients having sarcoma or normal patients. Principal component analysis (FIG. 6) shows that some of the patients at risk of pancreatic cancer have a binding profile clustering with patients having cancer. However, patients having pancreatitis cluster separately from patients having pancreatic cancer. Thus, binding profiles can be used as a predictor of cancer development in at risk patients and to distinguish pancreatitis from cancer.

Figure 7:
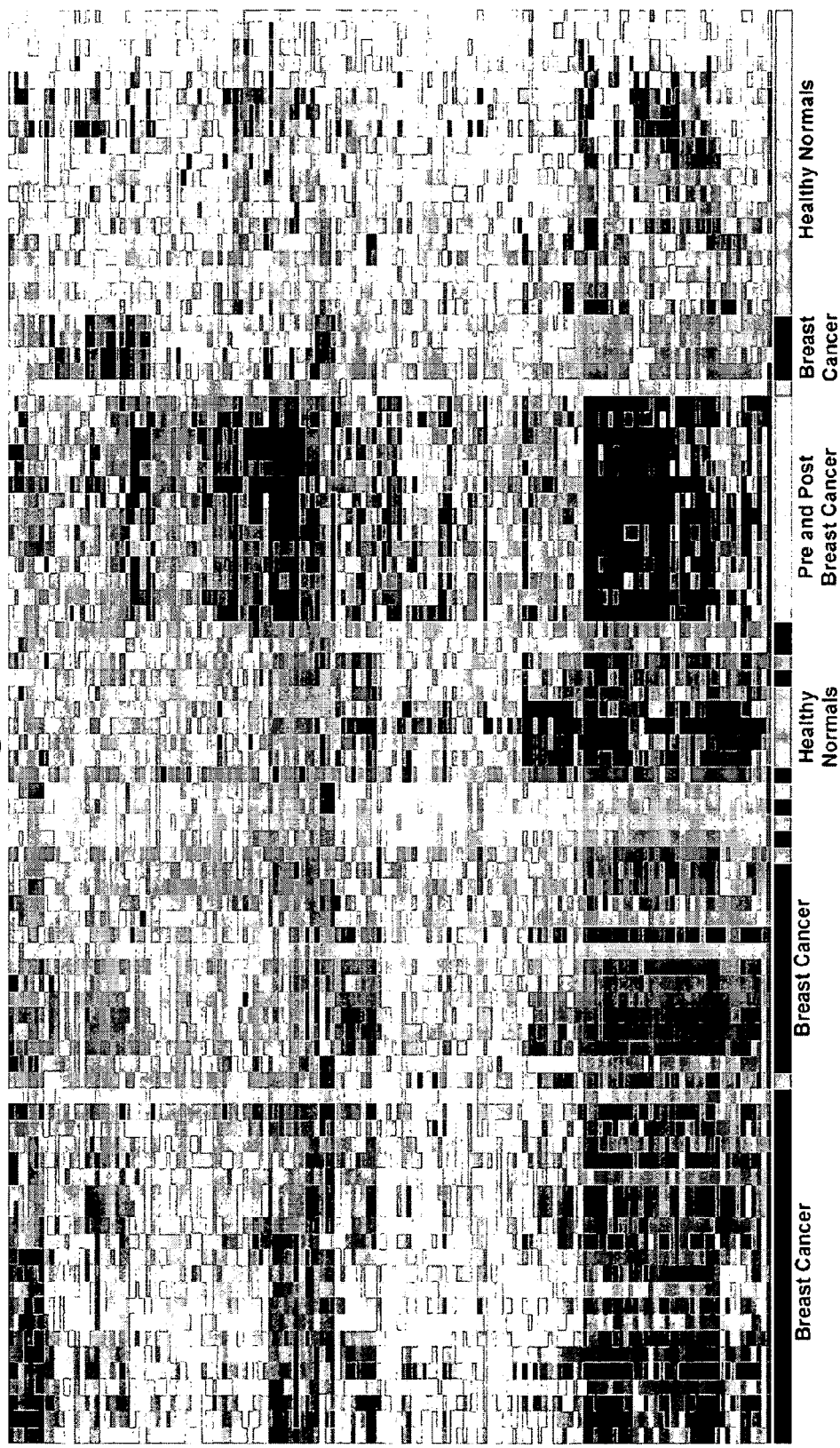
FIG. 7 compares binding profiles of normal volunteers, Breast Cancer patients, and patients at risk of breast cancer who clinically have had a second, different primary tumor following an initial remission of Breast Cancer.

FIG. 7 compares binding profiles of normal patients, breast cancer patients, and patients at risk of breast cancer. The binding profiles distinguish breast cancer patients from normals, and classify pre-symptomatic cancer patients as having a breast cancer pattern years before detection of a tumor. The binding profiles of pre-symptomatic samples also differ from normals because of their lack of variability (a hallmark of normals).

Example 4

A sublethal influenza A/PR/8/34 infection of $1\times10^4$ viral particles was used to impart protection against a later lethal challenge of the same strain in BALB/c mice. Lethal challenge using 2-5 mean lethal doses of influenza A/PR/8/34 occurred on day 35. The resulting immune response was protective as no overt clinical signs of infection or weight loss were observed following challenge. Portions of this example have been reported by the inventors in Lugutki et al, Vaccine (May 5, 2010) PMID: 20450869.

Serum from live influenza immunized mice were run on the arrays. At day 14, the influenza-specific IgG ELISA titer was 1:102,400 indicating virus specific antibodies were present. Difference in antibody binding to the CIM10K array could be detected 14 days after immunization confirming that a change in humoral immune status could be detected. Comparison of the 271 peptides recognized at least two-fold greater by live influenza immunized mice did not overlap with the 542 peptides recognized at least two-fold more than age matched naïve mice immunized 29 days previously with *F. tularensis* LVS. Therefore an array of 10,000 random peptides are sufficient generate immunosignatures can distinguish between two infections.

Figure 8:
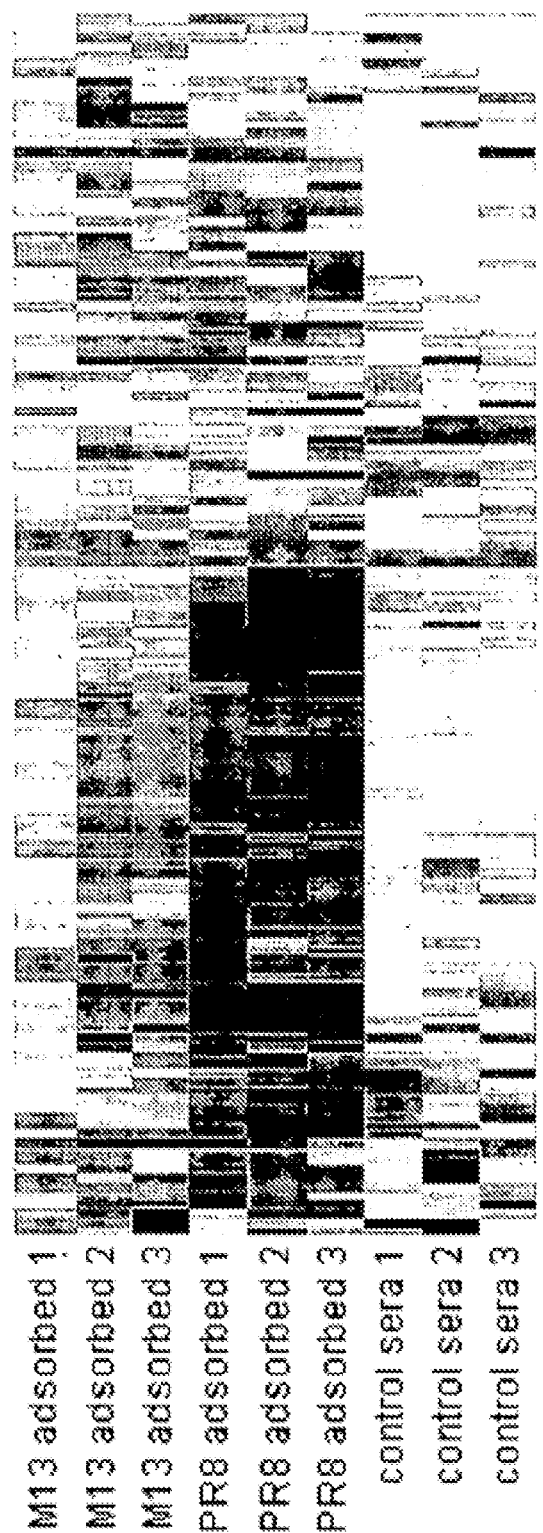
FIG. 8 shows a pattern for influenza in mice blocked using whole virus particles pre-adsorbed to antisera from infected mice. This same pattern was not blocked by an irrelevant virus.

Mice were infected with influenza and 21-day antisera was tested for an immunosignature pattern. We found a specific influenza pattern in mice that could be blocked using whole virus particles pre-adsorbed to antisera from infected mice but not by an irrelevant virus (M13) (FIG. 8). Comparison of the absorbed sera in an ELISA revealed a reduction in IgG reactivity for the virus from an endpoint titer of 512,000 for the unabsorbed 387 sera to less than 500 for the virus absorbed sera. Reactivity for the possible to determine antibody reactivities that declined on immunization in a standard ELISA.

To determine whether these peptide populations were the result of the primary immunization or a combined effect of immunization and challenge, the recognition of these peptide populations were compared in immunized only mice. At 118 days post-immunization, immunized only mice had a mean fold increase from day 0 of $5.18\pm3.57$ for the 283 time stable peptides compared to immunized and challenged mice at 98 days post-challenge which had a mean fold increase of $4.19\pm2.55$ from day 0. At the same time point, the suppressed peptides had a similar fold change 350 from day 0 of $0.39\pm0.29$ in the immunized mice and $0.36\pm0.098$ in immunized and challenged mice. Taken together these results demonstrate that a lasting and complex immunosignature is generated upon initial infection and it is unique to the infecting organism.

We sought to determine whether the immunosignature on the CIM10K was transient or remained consistent over time and correlated to the antibody titer in a virus specific ELISA. The immunized animals were followed for 211 days post-challenge and the changes to peptide recognition levels by serum antibodies on the CIM10K array observed. In a standard ELISA against whole virus, the IgG titer rose to 819,200 by the day of challenge and remained elevated and unchanged during the post-challenge observation period. An "expression pro-file" reflecting the changes in bulk IgG ELISA titer was established in the Gene Spring software package. Comparison of the relative fluorescence intensities of recognized peptides to the profile identified peptides whose intensities over time matched the defined profile with a Pearson correlation of greater than 0.9. Profile analysis was similarly used to identify sets of peptides whose recognition was increased after immunization but diminished after challenge and those that were initially recognized at day 0 but were no longer recognized following immunization. At 118 days post-immunization, immunized only mice had a mean fold increase from day 0 of $5.18\pm3.57$ for the 283 time stable peptides compared to immunized and challenged mice at 98 days post-challenge which had a mean fold increase of $4.19\pm2.55$ from day 0. At the same time point, the suppressed peptides had a similar fold change from day 0 of $0.39\pm0.29$ in the immunized mice and $0.36\pm0.098$ in immunized and challenged mice. Taken together these results demonstrate that a lasting and complex immunosignature is generated upon initial infection and it is unique to the infecting organism.

We sought to determine whether the antibody immunosignature on the CIM10K correlated to the immunizing dose of virus. Groups of BALB/c mice had increased weight loss and recovery time which correlated to increased infectious dose. Mice were allowed to recover to pre-infection weight and serum was collected at day post-infection. Bulk IgG endpoint titers against the virus were indistinguishable between groups with an endpoint titer of 102,400 for all groups. This suggests that the maximum detectable response in an ELISA was quickly reached at the lowest immunizing dose. Computer analysis of the CIM10K immunosignatures revealed 516 peptides that generally increased with infectious dose, of which a subset of 65 rose sharply. Comparison of the time stable peptides to the dose responsive peptides showed an overlap of 39 peptides, three times that predicted by chance. These results demonstrate that immunosignature has greater resolving power than whole virus ELISA in terms of distinguishing the infectious dose.

Antibody responses to infection or vaccine can be measured by ELISA for each of the responding isotypes. We sought to determine whether or not the antibody reactivity on the random CIM10K peptide array could detect changes in antibody isotype. The IgM, IgA, IgG1, IgG2a and IgG3 immunosignatures were determined using serum samples from day 0 and day 28. Peptides recognized with relative fluorescence intensities greater than array features containing only buffer were analyzed. Populations of peptides recognized by the different isotypes are presented as a modified Venn diagram in FIG. 5. Peptide overlap sets containing more members than that predicted by chance overlap for equivalent sized lists were limited to certain overlap regions suggesting potential class switching from IgM and overlap with IgA indicating the switch to IgA that is expected in containing an airways infection. Fitting an immune response to a viral infection, the IgG subtype response was predominantly IgG2a where nearly half the array was increasingly over two-fold recognized by day 28 serum. Conversely, only 144 peptides were over two-fold recognized by IgG1 antibodies. This demonstrates that the immunosignature can be subdivided based on antibody isotypes which reflects the pathogenesis of the responsible agent. In contrast to the ELISA protocol, each isotype assay only required 0.5 µl serum.

We sought to determine whether or not the immunosignature was consistent between biological replicates. Additional groups of BALB/c mice were separately obtained approximately 2 months apart and independently infected with the sublethal dose used for immunization. Weight loss was consistent for all groups and at day 28 each group had a bulk IgG titer of 19,200. To address the consistency of the immunosignature across independent infections, day 28 sera from the three infections were allowed to bind the CIM10K array and fluorescence intensities compared. For all peptides on the array the Pearson correlation was 0.94 between infections. The time stable peptides had Pearson correlations of 0.904, 0.936 and 0.912 between infections. Compared to the bioinformatic average of all naïves tested, the three infections had similar fold increase values for the 283 time stable peptides (2.23±1.22, 2.88±1.0, and 1.93±0.97). These results demonstrate that the immunosignature is consistent across biological replicates of infection and across technical replicates. There is no loss of consistency between biological replicates when using random peptides in place of the authentic virus antigen.

Naïve inbred mice provide a relatively empty canvas on which to develop an antibody repertoire. We sought to determine if a consistent immunosignature could be distinguished in a diverse human population. The immunosignature to the human seasonal 2006-2007 influenza vaccine was evaluated as our model. Individual sera from seven human donors were allowed to bind the array and analyzed for differences in peptide recognition between pre-immune and day 21. Donors were determined to have serum IgG antibodies in an ELISA against the 2006-2007 seasonal vaccine. For the human donors the median day 0 IgG titer was 1:3200 and the median day 21 titer was 1:12,800. Analysis identified 30 peptides that significantly increased (p<0.01) on day 21 at least 1.3 times that of the pre-immune or donor background values. These 30 peptides were sufficient to clearly distinguish the immune and pre-immune classes using principle component analysis. Four principle components were identified of 38%, 23%, 13% and 9% variance, respectively. One patient was separated across the X-axis for both immune and pre-immune samples and may suggest a low responding immune system. The remaining patient samples were still distinguished by class when this patient was excluded from the analysis. These results demonstrate that the immunosignature of serum antibodies are informative.

It would be of great advantage to know what antigen had produced a diagnostic antibody. We have developed a protocol that allows this "backtracking" from the array peptide to the natural protein. Basically the reactive peptide is resynthesized on Tentagel Beads. The beads are reacted with the serum to affinity purify the antibody. The antibody is then released from the beads. This antibody can then be used against an extract to identify the protein. Another method would be to make a phage library of antibodies from the individual producing the immune response and isolate the phage-ab binding the peptide of interest.

Figure 9:
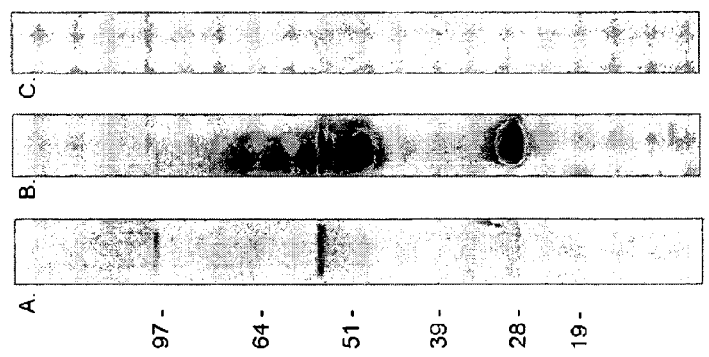
FIGS. 9A, B and C show that an antibody pulled-down using peptides from the immunosignaturing microarray can detect the influenza particles.
FIG. 9B is a positive control showing where the antibody is detecting influenza particles.
FIG. 9C is a negative control pull-down from the beads alone.

An array peptide that showed strong reactivity against influenza but not normal mouse sera was selected to pull down antibodies against influenza specifically. The pull-down was done using 10 ug peptide chemically conjugated to Tentagel® beads. Antibodies were eluted with pH 2.0 glycine, then immediately neutralized. PR8 was immobilized on nitrocellulose and probed with the pulled-down antibodies. FIGS. 9A, B and C show the pulled-down antibody detecting PR8 particles, a positive control anti-PR8 antibody picking up the virus particles, and a negative control pull-down from the beads alone. The data indicate we pulled down the appropriate anti-PR8 antibody with the peptide from the microarray that showed the strongest reactivity to PR8-infected mice.

The immunosignature can be used to classify the recipient based on immunogen. Protection against influenza infection in a murine model is largely based on the generation of neutralizing antibodies. To test the ability of the immunosignature to distinguish a protective antibody response from a non-protective antibody response, the archived serum samples were used to probe the CIM10K array. A random number generator was used to assign samples to either set A or set B so that each set contained four A/PR/8/34 infected groups, five KLH immunized groups and seven naïve groups. This way either set could be used as the training set and selected peptides used to predict the members of the second set. Peptides were selected from the CIM10K using the association algorithm in Genespring 7.3. For training on set A, 515 peptides with a median p value of $2.32 \times 10^{-7}$ were identified. TSupport vector machines were used to test the ability of the 515 to predict the immunogen used. When set A was used to train for prediction of set B, 81.3% of the samples were predicted correctly. When set B was used to train for prediction of set A using the 515 peptides, 93.8% of the samples were predicted correctly.

As a test of the validity of the methodology to select predictive peptides, association algorithm was applied to set B to identify 518 peptides with median p values of $6.34 \times 10^{-5}$ for set B and $2.00 \times 10^{-5}$ for set A. Support vector machines trained on set B to predict set A identified 81.3% of the samples correctly and training on set A to predict set B identified 75% of the samples correctly. The identified lists of associated peptides from set A and set B overlapped by 122 peptides which is greater than predicted by chance overlap. The overlap list predicted 81.3% of the samples correctly regardless of which set was the training set or the test set.

Immunization with homologous and heterologous vaccines produce different antibody responses and degrees of protection to challenge with Influenza A/PR/8/34.

We next sought to determine whether the immunosignature had the power to distinguish similarly composed vaccines and stratify them based on outcome. As our model vaccines we used inactivated A/PR/8/34 as the homologous "good" vaccine and the 2006/2007 & 2007/2008 human seasonal influenza vaccines as the heterologous "bad" vaccines. Efficacy was determined in a murine lethal challenge model of influenza A/PR/8/34 infection. At day 40, serum IgG titers were measured. Mock immunized mice showed no reactivity for either A/PR/8/34 or the seasonal vaccines. Mice immunized with inactivated virus had IgG titers for all three antigens with a lower titer for the 2007/2008 seasonal vaccine components. The seasonal vaccines showed cross reactivity for each other with low reactivity for the A/PR/8/34 virus. Cross reactivity between seasonal vaccines is expected due to the inclusion of A/Wisconsin/67/2005 and B/Malaysia/2506/2004 in both vaccine compositions. The heamagglutanin and neuraminidase sequences from A/PR/8/34 do have some homology to the A/New Calcdonia/20/99 and A/Solomon Islands/3/2006 sequences but appear to have generated a unidirectional cross reactivity in the ELISA.

Pooled serum samples were also used to probe the CIM10K. The association test was applied to the array data and 367 peptides associated with immunogen were identified. These peptides are sufficient to distinguish the groups with an average intergroup p value of $3.9 \times 10^{-5}$. This demonstrates that the CIM10K has the resolving power to distinguish closely related immunogens from each other based on the humoral immune response. To account for the heterosubtypic crossreactive antibodies observed in the ELISA the three inactivated vaccines were compared to mock immunized. This comparison yielded 116 peptides with a p<0.01 of which 54 were increased in the vaccines over mocks. Relative intensity levels of the 54 peptides were comparable between groups. This list of peptides was tested in support vector machines for the ability to separate the A/PR/8/34 and the KLH immunized mice. For the combined sets A and B, no crossvalidation error was observed suggesting this set is likely composed of influenza specific cross reactive antibodies.

At challenge on day 42, mice immunized with inactivated A/PR/8/34 survived without clinical signs of illness. Mice immunized with the seasonal vaccines became sick and had 60% survival in the 2006/2007 seasonal vaccine group and 70% survival in the 2007/2008 seasonal vaccine group. Surviving mice in the seasonal vaccine groups recovered to prechallenge weight. This demonstrates that the vaccines are not equally protective in challenge with A/PR/8/34. Taken together these data demonstrate that the different vaccines generate distinctive immune responses as determined by whole virus ELISA and CIM10K and have different protective outcomes.

The immunosignature of live immunization and subsequent challenge can predict the efficacy of inactivated vaccines. To evaluate if the immunosignature of a naturally acquired infection and resistance to subsequent infection could predict the efficacy of an inactivated or subunit vaccine, we examined microarray data from mice infected with a sublethal dose of A/PR/8/34 and subsequently challenged with a lethal dose of the same strain 35 days later. We first asked if the peptides that were recognized by serum antibodies present in immune mice at the time of challenge were capable of predicting vaccine efficacy. 50 peptides significantly (twofold increase with a p<0.01) increased from day 0 to day 28. Support vector machines trained on the immune and naïve mice (day 28 and day 0) for testing on the model vaccine trail were incapable of distinguishing the groups, suggesting an amplification of protective clones was required for survival in a subsequent challenge.

To test this hypothesis, we asked if peptides increasing between pre and post challenge could predict the efficacy of the inactive vaccines. Analysis identified 163 peptides as increasing greater than twofold from pre to post challenge with a p value less than 0.05. Support vector machines trained on the immune and naïve samples (day 28 and 0) were able to predict the challenge outcome in terms of success defined by no change in health status (inactive A/PR/8/34) or unsuccessful defined by illness (seasonal vaccines and mock). This demonstrated that the ability of the immunosignature to identify the antibody reactivities responsible for protection to a second exposure can predict the efficacy of a subunit or inactivated vaccine.

Example 5

Multi-Disease Classifier

About 875 individual samples from individuals with infectious disease, autoimmune disease, cancer, Alzheimer's and other diseases were analyzed independently on a 10,000 peptide array. The binding profiles were initially represented as a heat map as for other profiles (FIG. 10A). Principal component analysis of the binding profiles for different diseases is shown in FIG. 10B. Each of the diseases has a distinguishable profile. Although inflammation is a major component in many of the diseases, it is not a major contributor to their binding profiles, which remain predominantly distinct with a classifier error below 10%

Example 6

The following table summarizes the results from several tests on clinical samples. FP (false positive), FN (false negative), AUC (area under a ROC curve, a measure of accuracy of diagnosis).

| Class | Disease | FP | FN | AUC | # disease samples |
|---|---|---|---|---|---|
| Pre-disease (pre-symptomatic) | panIN (pre-panc. Cancer) | 0 | 0 | 1 | 8 human |
| Vaccine and challenge | Influenza | 0 | 0 | 1 | 15 human, 4 years |
|  |  | 0.001 | 0 | 0.999 | 120 mice |
|  | Pancreatic Cancer | 0.2 | 0 |  | 8 human |
| Infectious disease | Valley Fever (Cocci) | 0 | 0 | 1 | 40 human |
|  |  | 0 | 0 | 1 | 9 dog |
|  |  | 0 | 0 | 1 | 60 mice |
|  | Q-Fever (*Coxiella*) | 0 | 0 | 1 | 30 rabbit |
|  | *Tularemia tularensis* | 0 | 0 | 1 | 21 mice |
|  | *Rickettsia rickettsii* | 0 | 0 | 1 | 37 mice |
|  | Glanders (*B. mallei*) | 0 | 0 | 1 | 26 mice |
| Chronic | Asthma IgG | 0 | 0 | 1 | 25 human |
|  | Asthma IgE | 0 | 0.01 | 0.97 | 25 human |
|  | Asthma IgA | 0 | 0 | 1 | 6 human |
| Autoimmune | Lupus | 0 | 0 | 1 | 60 mice |
|  | Type I diabetes | 0.13 | 0.02 | 0.80 | 56 human |
| Cancer | Glioblastoma | 0 | 0 | 1 | 10 human |
|  | Breast | 0.01 | 0.009 | 0.986 | 156 human |
|  | Multiple primary | 0 | 0 | 1 | 7 human |
|  | Pancreatic cancer | 0.06 | 0.02 | 0.92 | 122 human |
|  | Lung | 0 | 0.11 | 0.81 | 60 human |
|  | Myeloma | 0 | 0 | 1 | 15 human |
|  | Ovarian | 0 | 0 | 1 | 6 human |
|  | Esophageal | 0 | 0 | 1 | 2 human |
| Other | Transplant | 0 | 0 | 1 | 6 human |

Example 7

Epitope Mapping

Motif finding algorithms are able to find subtle patterns in sets of unaligned sequences. These algorithms may be classified in two main categories: deterministic and optimizing. Deterministic algorithms exhaustively search a sequence set for motifs fitting a well defined set of criteria. Some popular implementations of deterministic motif finding algorithms are TEIRESIAS or PRATT (Rigoutsos, *Bioinformatics.* 14, 55-67 (1998); Jonassen (1997) *Comput. Appl. Biosci.* 13, 509-22).

The optimizing algorithms represent the motif probabilistically and try to maximize a scoring function. The optimization can be preformed stochastically such as using Gibbs motif sampling or by expectation maximization as implemented in MEME (Bailey (2006) *Nucleic Acids Res.* 1, W369-7316).

An optimization approach is preferred when it is not known what criteria the motif should fulfill. The GLAM2 implementation of the Gibbs motif sampling algorithm will be used here because it allows for gaps (Frith (2008). *PLOS Comput Biol.* 4, e1000071.17).

An alternative to finding a motif among the peptides is to compare the peptides one at a time to the antigen sequence(s). The algorithm implemented in the RELIC MATCH 5 program compares each peptide sequence to the target protein sequence in five amino acid windows, and scores each window for similarity (18). The scores for all of the peptides are added up across the protein sequence to predict potential small molecule binding site. A similar approach can be used for predicting antibody recognition sites from dissimilar peptide sequences selected in a peptide microarray experiment.

Typically, epitope mapping is performed to identify the specific part of a protein target that is recognized by the antibody. A similar approach can be used to identify an unknown protein target of an antibody. This approach can be used in identifying the antigenic proteins in a pathogen, targets in an autoimmune disease, or discovering the cause of an unknown infection.

Antibodies with known epitopes were purchased from Labvision (Fremont, Calif.) and Abcam (Cambridge, Mass.). Mice were immunized with keyhole limpet hemocyanin (KLH) conjugated peptides and sera was obtained at day 35. After slides were passivated with 0.014% Mercaptohexanol, antibody was diluted to 100 nM or sera was diluted 1:500 in 3% BSA, 0.05% Tween, PBS. Antibodies were incubated with slides for 1 hour at 37 C in Agilent Chambers with rotation. Slides were washed three times with TBS, 0.05% Tween and three times with diH2O. The incubation and wash procedure was repeated with a biotinalyted secondary antibody (Bethyl Laboratoreis, Inc. Montgomery, Tex.), then with Alexa-555 labeled Streptavadin (Invitrogen, Carlsbad, Calif.).

| Name | Isotype | Num of AA | pI | Hydropathicity |
|---|---|---|---|---|
| mAb1 | IgG1 | 9 | 3.56 | −0.9 |
| mAb2 | IgG1 | 9 | 8.75 | −0.044 |
| mAb3 | IgG1 | 5 | 9.76 | −0.02 |
| mAb4 | IgG2a IgG2b | 6 | 5.84 | 0.517 |
| mAb5 | IgG1kappa | 6 | 4.67 | −0.583 |
| pAb1 polyclonal | IgG | 20 | 4.21 | −0.185 |
| pAb2 polyclonal | IgG | 20 | 4.43 | −1.245 |
| pAb3 polyclonal | IgG | 20 | 6.4 | 0.87 |
| pAb4 polyclonal | IgG | 20 | 8.64 | −0.13 |
| pAb5 polyclonal | IgG | 20 | 3.49 | −0.315 |

Negative control arrays with no primary antibody or naïve mouse sera were also run for comparison. At least three replicate arrays were run for each antibody.

Antigen specific antibodies were absorbed from sera by binding to KLH immobilized on nitrocellulose membrane. A one by six centimeter nitrocellulose membrane was placed in a 15 ml conical tube with 1.0 mg/ml KLH in 2.0 ml PBS. The membrane was washed three times in TBST and incubated with 1.0% BSA in TBST for at least one hour or until used. After washing three times in TBST, the membrane was placed into 2.0 ml of sera diluted 1:500 in 3% BSA, 0.05% Tween, PBS buffer. Reactivity of sera for KLH was tested in an ELISA. Sera were considered absorbed when no reactivity for KLH was detected at the 1:500 dilution.

Negative control signals were subtracted from antibody signals to remove the contribution of the secondary binding. The top 500 peptides in fluorescent intensity were selected for each antibody. The number of times each peptide occurs in one of the top 500 peptides lists was tabulated. Peptides appearing in five or more lists were eliminated as they are likely Fc binders or other nonspecific interactions. Peptides from the array were compared to the epitope sequences to identify those with sequence similarity. The epitope was expressed as a GLAM2 motif and was used in GLAM2SCAN to search against the peptides from the array inserted in strings of cysteines, with an alphabet of equal amino acid frequencies. Peptides were sorted by the highest scoring match and lists of the best matching peptides were created. These lists were compared with lists of peptides that most strongly bind to each peptide and the proportion of overlap was examined. Test datasets were generated for the monoclonal antibodies by randomly selecting sequences from human Swissprot and then randomly selecting a window of that sequence the same length as the epitope sequence. Two hundred negative examples were generated for each monoclonal. One thousand random peptides were generated as the negative examples for the polyclonal antibodies with equal frequencies of the nineteen amino acids (cysteine was not included as in the arrays). All of these sequences were inserted within a string of seventeen cysteines on each side to allow peptides to be aligned overhanging the test sequences.

Motifs were generated from the peptide lists using GLAM2, with a starting width of five amino acids, 1,000,000 iterations without improvement, 10 runs, and an alphabet of equal proportions of the 20 amino acids. GLAM2SCAN was used to search the corresponding test sets for sequences matching the motif with the alphabet set as the default protein alphabet for the monoclonal antibodies or equal amino acid frequencies for the polyclonal antibodies.

GLAM2SCAN output is the score for each place the motif matches in the test sequence set. The test sequences were ranked by the highest score match within each sequence. The RELIC Fastaskan program was used to align the binding peptides to the test dataset.

The top 500 specific peptides were uploaded as the affinity selected peptides and the corresponding test dataset was uploaded as the FASTA file. Random peptides were not subtracted. Fastaskan compares each five amino acid window of the test sequence with the selected peptide sequence and summing scores of the alignments above a threshold. It outputs a score for each test sequence corresponding to the window of maximum similarity between the peptides and that sequence.

For both the GLAM2SCAN and the RELIC analysis, the rank of the true epitopes was compared to the test sequences using ROC analysis. A Matlab script to calculate the true positive and false positive rate for each score cutoff was obtained from world wide web //theoval.cmp.uea.ac.uld~gcc/matlab/roc/ and modified to smooth tied scores. The area under the ROC curve was also calculated using a Matlab script from the same website. The area under the curve is used to predict the probability of finding an epitope in a database of a given size. We will assume positive and negative examples will be selected from a database of a fixed size without replacement weighted by the probability that a positive is chosen over a negative as estimated by the area under the curve.

To evaluate the peptide microarray platform, examples of known epitope antibodies were required to generate a test dataset. Five monoclonal antibodies with known linear epitopes, and five examples of anti-peptide polyclonal mouse sera raised against peptides selected from the array were used as the test set. The monoclonal antibodies were found to bind to a median of 64.1% (range 37.6%-74.9%) of the random peptides above the slide surface background and secondary only controls. Polyclonal sera showed similar peptide reactivity with a median of 63.6% (range 54.0%-68.6%). Replicate slides had an average Pearson correlation of 0.785 for monoclonals and 0.764 for polyclonals. A heatmap showed that each antibody has a distinct binding pattern on the array. Although there is some overlap between the peptides bound by each antibody, about 22% of the top 500 peptides recognized by each antibody are not recognized by the other nine antibodies tested. The uniqueness of the peptides recognized by each antibody implies that the peptide sequences may contain information about antibody specificity.

Each peptide sequence was scored for similarity against each protein sequence. Most of the peptides bound by the antibodies did not show strong sequence similarity to the epitope. However, there was some enrichment for sequence similar peptides among the binders. Most of the peptides bound are mimotopes rather than having any obvious similarity to the epitope.

To assess the predictive power of these sequences the alignment of the peptides to the epitopes was compared to their alignment with a set of negative examples. The RELIC alignment program was able to align binding peptides to all of the monoclonal epitopes and 62.7% of the negative examples. The true epitopes had an average score of 14.3 whereas the negative examples had an average score of 5.9. The ROC analysis found an area under the curve of 0.87 indicating that a true epitope has an 87% chance of having a higher score than randomly selected negative example. All of the polyclonals also had positive peptide alignment scores as well as 86.5% of the positive examples. The true epitopes had an average score of 14.7 whereas the negative examples had a score of 15.2. The ROC analysis (FIG. 5) indicates that a positive example has a 46% chance of having a higher score than a negative example based on the area under the curve. The monoclonal epitopes were predicted well by this method, whereas the polyclonal predictions were similar to chance. An algorithm capable of detecting subtle patterns may be able to garnish predictive power from these peptide sequences. Convergent motifs were identified for all of the antibodies using GLAM2. The motifs for the monoclonal antibodies ranged from three to five amino acids in width. The polyclonal motifs were four to five amino acids wide. The monoclonal motifs matched the epitope sequences with an average score of 3.5, whereas the negative examples had an average score of −3.7. Polyclonal motifs matched the immunizing peptide with an average score of 3.8 whereas the negative examples had an average score of 3.7. The ROC analysis demonstrates that the monoclonals epitopes have an 89.8% chance of being scored higher than the corresponding negative examples in the motif analysis while the polyclonals have a 67.9% chance of scoring higher than the negatives. The motif finding approach demonstrated predictive power on both datasets.

|  | binders | aligner | Both | expected | ratio | % of binders align |
|---|---|---|---|---|---|---|
| AbCamHA | 350 | 181 | 6 | 5.88 | 1.02 | 1.7% |
| DM1A | 391 | 379 | 21 | 13.75 | 1.53 | 5.4% |
| LNI(132 | 354 | 96 | 2 | 3.15 | 0.63 | 0.6% |
| P53Ab1 | 379 | 188 | 36 | 6.61 | 5.45 | 9.5% |
| P53Ab8 | 369 | 365 | 6 | 12.50 | 0.48 | 1.6% |
| Neg1 | 258 | 722 | 26 | 17.28 | 1.50 | 10.1% |
| Rco4 | 258 | 755 | 26 | 18.07 | 1.44 | 10.1% |
| Rco3 | 263 | 710 | 18 | 17.32 | 1.04 | 6.8% |
| Rco2 | 274 | 742 | 22 | 18.86 | 1.17 | 8.0% |
| Rco1 | 267 | 699 | 21 | 17.31 | 1.21 | 7.9% |
| average | 316.3 | 483.7 | 18.4 | 13.07 | 1.55 | 6.2% |

To test if combining the two approaches may improve the predictive ability, the scores from the RELIC analysis and the GLAM2 analysis were each scaled to have a minimum score of zero and a maximum score of one and averaged. The ROC analysis was performed on the averaged scores. The area under the curve was 0.92 for the monoclonals and 0.69 for the polyclonals. Based on the probability estimated from the ROC analysis, there is about a 70% chance of finding a monoclonal epitope in the top ten windows out of a one hundred amino acid protein. There is about a 21% chance of correctly identifying a polyclonal epitope in a small virus among the top 100 hits out of a possible 1000 amino acid database, which is a two-fold enrichment.

Example 9

General Materials and Methods

Preparation of the Random Peptide Microarrays

The random CIM10,000 f microarray consists of 10,000 20-residue peptides of random sequence, with a C-terminal linker of Gly-Ser-Cys-COOH. Each peptide was manufactured by Alta Biosciences, Birmingham, UK based on amino acid sequences we provided. Random sequences were provided by custom software (Hunter, Preston and Uemura, Yusuke, The Biodesign Institute). Nineteen amino acids (cysteine was excluded) were selected completely at random in each of the first seventeen positions with GSC as the carboxy-terminus linker. The synthesis scale was 2-5 mg total at ≥70% purity with 2% of the peptides tested at random by mass spectrometry. Dry peptide was brought up in 100% N,N' dimethyl formamide until dissolved, then diluted 1:1 with purified water at pH 5.5 to a master concentration of 2 mg/ml. The original 96-deep-well plates were robotically transferred to 384-well potting plates, and the peptides were diluted to a final spotting concentration of 1 mg/ml concentration in phosphate buffered saline at pH 7.2. High-quality pre-cleaned Gold Seal glass microscope slides were obtained from Fisher (Fair Lawn, N.J., cat#3010). Each slide was treated with amino-silane, activated with sulfo-SMCC (Pierce Biotechnology, Rockford, Ill.) creating a quality-checked maleimide-activated surface designed to react with the peptide's terminal cysteine. During spotting, we employ a Telechem Nanoprint 60 using 48 Telechem series SMP2 style 946 titanium pins. Each pin is allowed to spot approximately 500 pL of 1 mg/ml peptide per spot, which is estimated by allowing for pin trajectory, surface dwell time, and the amount of liquid each pin holds. The spotting environment is 25° C. at 55% humidity. Each peptide is spotted twice per array; the arrays are spotted in an orange-crate packing pattern to maximize spot density. Fluorescent fiducials are applied asymmetrically using Alexa-647, Alexa-555, Alexa-488 and Alexa-350-labeled peptides. The fiducials are used to align each subarray during image processing. The printed slides are stored under argon at 4° C. until used. Quality control consists of imaging the arrays by laser scanner (a Perkin-Elmer ProScanArray HT, Perkin Elmer, Wellesley, Mass.) at 647 nm to image the spot morphology. If the batch passes this test, further testing of randomly selected slides with known proteins and antibodies allows QC of reproducibility. Array batches that fail to meet an array-to-array variability of 30% total CV are discarded. Data extraction is accomplished using GenePix Pro 6.0 (Molecular Devices Inc., Sunnyvale, Calif.).

Probing the Random Peptide Microarrays with Serum Antibodies.

Slides were processed using a Tecan HS4800 Pro Hybridazation station with a protocol adapted to antibody binding. General settings were wash duration of 30 sec at 11.0 ml/min and sample agitation was set to high. Arrays were blocked with 1×PBS, 3% BSA, 0.05% Tween 20, 0.014% mercaptohexanol for 15 min at room at 23° C. Arrays were probed with 170 µl of serum diluted at 1:500 in incubation buffer (3% BSA, 1×PBS, 0.05% Tween 20) for 1 hour at 37° C. Slides were washed between with TBST. Bound IgG was detected using biotinylated anti-mouse IgG (Bethyl Laboratories, Montgomery, Tex.) for 1 hour at 37° C. The anti-alpha chain secondary antibody was detected using Alexafluor 649 labeled streptavidin at 5.0 nM in incubation buffer for 1 hour at 37° C. Final washes in TBST and distilled water were done to remove residual salt. Slides were dried by on board nitrogen flow for 5.0 min. Images were recorded using an Agilent 'C' type scanner at both 543 nm and 633 nm.

Analysis of Random Peptide Microarray Data.

Statistical analysis of microarray data was done with GeneSpring 7.3.1 (Agilent, Inc., Palo Alto, Calif.) by importing image-processed data from GenePix Pro 6.0 (Axon Instruments, Union City, Calif.). Calculations based on the GenePix prepared gpr text files were done on the median signal intensity per spot. Poor quality spots were excluded from analysis by flagging as "absent" upon visual inspection. Prior to analysis, each array was normalized to the 50$^{th}$ percentile to eliminate array to array variation and signal intensities of less than 0.01 were set to 0.01. Values from triplicate arrays were averaged and used in the analysis. Informative peptides were determined by comparing groups on a peptide to peptide basis. Peptides with a relative fluorescence intensity of 500 or greater and a p value <0.01 were selected. Further statistical analysis was conducted in MicroSoft Excel 2003 SP3 or in GraphPad Prism version 4.00 for windows (Graphpad Software, San Diego, Calif.). The principle component analysis feature in Gene Spring was used to distinguish serum samples based on selected gene lists. PCA was run using mean centering and scaling. Support vector machine analysis was run in GeneSpring using Fisher's Exact Test limited to 50 peptides, polynomial dot product order 1 and a diagonal scaling factor of 0 to generate cross validation errors and predict test sets.

Characterization of Archived Murine Serum Samples.

To test whether an immunosignature correlates with vaccine efficacy, even if protection is driven by a small number of neutralizing antibodies, a sublethal influenza A/PR/8/34 infection was used as a model protective vaccine and KLH immunization as a model non-protective vaccine. KLH was chosen due to its ability to generate an equivalently robust humoral immune response. The average IgG titer against whole virus in A/PR/8/34 infected mice was 819,000 and 800 for KLH immunized mice. Lethal challenge using 2-5 mean lethal doses of influenza A/PR/8/34 occurred on day 35. The immune response generated by the sublethal infection was protective as no overt clinical signs of infection or weight loss were observed following challenge. Mice immunized with KLH contained either KLH alone or unrelated peptide-KLH conjugates adjuvanted with Alum. The average anti-KLH IgG titer was 819,000 in KLH immunized mice and 1,600 in A/PR/8/34 immunized mice. Following challenge at day 35, KLH immunization imparted no benefit over naives. This indicates that the model vaccines had equivalently strong immune responses for their respective immunogen with little ELISA cross-reactivity and no protection due to immunization with KLH.

What is claimed is:

1. A method of determining a status of a subject, comprising:
   (a) contacting a sample from the subject comprising at least 100 different antibodies, wherein not all of the at least 100 different antibodies are autoantibodies, with an array of immobilized different peptides of between 10-30 amino acids in length, wherein each different peptide has a unique amino acid sequence, each of the immobilized different peptides occupying different features of the array, wherein at least 50 of the immobilized different peptides have dissociation constants of between 1 mM and 1 µM to at least one antibody in the sample, and wherein the array comprises at least 100,000 immobilized different peptides;
   (b) detecting binding of the immobilized different peptides in the array to antibodies of the sample to obtain a binding profile of the sample, wherein the binding profile is the aggregate effect of the sample binding to the immobilized different peptides occupying different features of the array; and
   (c) analyzing the binding profile by comparing the binding profile detected to a reference binding profile to determine the status of the subject.

2. The method of claim 1, wherein different molecules of a same peptide sequence within a feature of the array are spaced less than 6 nm apart.

3. The method of claim 1, further comprising identifying an antibody of the sample that binds to the immobilized different peptides.

4. The method of claim 3, further comprising detecting the identified antibody with a binding partner known to bind the antibody.

5. The method of claim 3, wherein the identified antibody is detected with a plurality of different binding partners known to bind the antibody.

6. The method of claim 4, wherein the binding partner is an antibody to the identified antibody or a peptide known to bind the identified antibody.

7. The method of claim 4, wherein the binding partner is one of the immobilized different peptides bound to the identified antibody in step (b) of claim 1.

8. The method of claim 4, wherein the binding partner is a synbody.

9. The method of claim 1, wherein the sequences of the peptides are randomly selected.

10. The method of claim 1, wherein the immobilized different peptides are selected without regard to the sample.

11. The method of claim 1, wherein the sequences of the immobilized different peptides have less than 90% sequence identity to a protein expressed by a genome.

12. The method of claim 1, wherein the contacting of the sample to the immobilized different peptides on the array is performed in the presence of a potential competitor of binding of the sample to the immobilized different peptides on the array.

13. The method of claim 12, wherein the competitor is a known binding partner of an antibody.

14. The method of claim 12, wherein the sample is a patient sample, and the potential competitor is a protein known to be associated with a disease affecting the patient.

15. The method of claim 1, wherein the sample is a patient sample.

16. The method of claim 15, wherein the patient is known or suspected to be suffering from a disease.

17. The method of claim 15, wherein the patient is known to be at risk of a disease but is not showing symptoms of the disease.

18. The method of claim 17, wherein the disease is an autoimmune disease.

19. The method of claim 17, wherein the disease is an infectious disease.

20. The method of claim 17, wherein the disease is a disease of the central nervous system (CNS).

21. The method of claim 14, wherein the sample is a blood, urine, or CNS sample from the patient.

22. The method of claim 1, wherein antibody(ies) of the sample are labeled prior to contacting with the array.

23. The method of claim 1, wherein binding of the peptides to antibody(ies) of the sample is detected using a secondary antibody.

24. The method of claim 23, wherein the secondary antibody is an isotype-specific antibody.

25. The method of claim 1, wherein binding of the peptides to antibody(ies) of the sample is detected by surface plasmon resonance (SPR) or mass spectrometry.

26. The method of claim 1, further comprising affinity purifying an antibody of the sample using a peptide determined to bind the antibody.

27. The method of claim 1, further comprising washing unbound antibody(ies) of the sample from the array, and dissociating bound antibody(ies) from the array.

28. The method of claim 1, wherein at least 100 of the immobilized different peptides have dissociation constants of between 1 mM and 1 μM to at least one antibody in the sample.

29. The method of claim 1, wherein at least 1000 of the immobilized different peptides have dissociation constants of between 1 mM and 1 μM to at least one antibody in the sample.

30. The method of claim 1, wherein at least 1% of the immobilized different peptides have dissociation constants of between 1 mM and 1 μM to at least one antibody in the sample.

31. The method of claim 1, wherein the subject's sample comprises at least one immunoglobulin isotype.

32. The method of claim 31, wherein the immunoglobulin isotype is IgG, IgA, IgM, IgE or combinations thereof.

33. The method of claim 1, wherein the subject's sample comprises the antibody repertoire of the subject.

\* \* \* \* \*